(12) United States Patent
Blomquist

(10) Patent No.: US 8,954,336 B2
(45) Date of Patent: Feb. 10, 2015

(54) SERVER FOR MEDICAL DEVICE

(75) Inventor: Michael L. Blomquist, Blaine, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 1011 days.

(21) Appl. No.: 11/066,425

(22) Filed: Feb. 22, 2005

(65) Prior Publication Data
US 2005/0246416 A1    Nov. 3, 2005

Related U.S. Application Data

(60) Provisional application No. 60/547,642, filed on Feb. 23, 2004.

(51) Int. Cl.
*A61N 1/18* (2006.01)
*A61N 1/20* (2006.01)
*A61N 1/22* (2006.01)
*A61N 1/28* (2006.01)
*G06F 19/00* (2011.01)
*H04L 29/08* (2006.01)

(52) U.S. Cl.
CPC ............ *G06F 19/3468* (2013.01); *H04L 67/12* (2013.01); *H04L 67/02* (2013.01)
USPC ................................................. 705/2; 607/5

(58) Field of Classification Search
USPC ............................................................ 705/2
See application file for complete search history.

(56) References Cited

U.S. PATENT DOCUMENTS

| | | |
|---|---|---|
| 2,968,804 A | 1/1961 | Buffington |
| 3,555,286 A | 1/1971 | Cote |
| 3,603,152 A | 9/1971 | Alibert et al. |
| 3,734,229 A | 5/1973 | Comer |
| 3,777,165 A | 12/1973 | Bryant et al. |

(Continued)

FOREIGN PATENT DOCUMENTS

| | | |
|---|---|---|
| CA | 2060151 | 8/1992 |
| CA | 2485024 | 11/2003 |

(Continued)

OTHER PUBLICATIONS

Merrit, R., "Wireless Hospital, Health Care Products on the Upswing," TechWeb, http://www.techweb.com/article/printableArticleSrc.jhtml?articleID=26803705, 2 pages (Jan. 7, 2004).

(Continued)

*Primary Examiner* — Hiep V Nguyen
(74) *Attorney, Agent, or Firm* — Patterson Thuente Pedersen, P.A.

(57) ABSTRACT

One aspect of the present invention is a server for communicating with a medical device. The server comprises a web browser process for communicating with a remote device and a pump interface process for communicating with a medical device. Another aspect of the present invention is a medical device. The medical device comprises memory configured to store data and a programmable circuit in electrical communication with the memory. The programmable circuit is programmed with a web server for communicating data with a remote device. Another aspect of the invention is a server for communicating with a medical device. The server comprises memory for storing data and a programmable circuit in electrical communication with the memory. The programmable circuit programmed with an interface for communicating with a medical device.

23 Claims, 7 Drawing Sheets

(56) References Cited

U.S. PATENT DOCUMENTS

| | | |
|---|---|---|
| 3,809,871 A | 5/1974 | Howard et al. |
| 3,923,060 A | 12/1975 | Ellinwood, Jr. |
| 3,942,526 A | 3/1976 | Wilder et al. |
| 3,985,133 A | 10/1976 | Jenkins et al. |
| 4,027,536 A | 6/1977 | Heggie |
| T961,004 I4 | 8/1977 | Horton |
| 4,080,967 A | 3/1978 | O'Leary |
| 4,091,550 A | 5/1978 | Schrenk et al. |
| 4,098,267 A | 7/1978 | Stein et al. |
| 4,137,913 A | 2/1979 | Georgi |
| 4,141,252 A | 2/1979 | Lodge |
| 4,146,029 A | 3/1979 | Ellinwood, Jr. |
| 4,174,637 A | 11/1979 | Mulzet et al. |
| 4,184,815 A | 1/1980 | Casson et al. |
| 4,191,184 A | 3/1980 | Carlisle |
| 4,210,138 A | 7/1980 | Jess et al. |
| 4,213,454 A | 7/1980 | Shim |
| 4,217,993 A | 8/1980 | Jess et al. |
| 4,236,880 A | 12/1980 | Archibald |
| 4,270,532 A | 6/1981 | Franetzki et al. |
| 4,279,188 A | 7/1981 | Scott |
| 4,280,136 A | 7/1981 | Kasbima et al. |
| 4,282,872 A | 8/1981 | Franetzki et al. |
| 4,299,218 A | 11/1981 | Knigge et al. |
| 4,299,541 A | 11/1981 | Ohara et al. |
| 4,308,866 A | 1/1982 | Jelliffe et al. |
| 4,309,993 A | 1/1982 | Brown |
| 4,311,377 A | 1/1982 | Matteson |
| 4,314,227 A | 2/1982 | Eventoff |
| 4,314,228 A | 2/1982 | Eventoff |
| 4,315,238 A | 2/1982 | Eventoff |
| 4,320,757 A | 3/1982 | Whitney et al. |
| 4,368,645 A | 1/1983 | Glenn et al. |
| 4,369,780 A | 1/1983 | Sakai |
| 4,370,983 A | 2/1983 | Lichtenstein |
| 4,373,525 A | 2/1983 | Kobayashi |
| 4,373,527 A | 2/1983 | Fischell |
| 4,385,630 A | 5/1983 | Gilcher et al. |
| 4,385,958 A | 5/1983 | Long |
| RE31,315 E | 7/1983 | Jenkins et al. |
| 4,392,849 A | 7/1983 | Petre et al. |
| 4,394,862 A | 7/1983 | Shim |
| 4,395,259 A | 7/1983 | Prestele et al. |
| 4,396,977 A | 8/1983 | Slater et al. |
| 4,398,542 A | 8/1983 | Cunningham et al. |
| 4,410,322 A | 10/1983 | Archibald |
| 4,413,314 A | 11/1983 | Slater et al. |
| 4,425,661 A | 1/1984 | Moses et al. |
| 4,431,425 A | 2/1984 | Thompson et al. |
| 4,443,218 A | 4/1984 | DeCant, Jr. et al. |
| 4,446,344 A | 5/1984 | Fiedler |
| 4,460,355 A | 7/1984 | Layman |
| 4,484,479 A | 11/1984 | Eckhardt |
| 4,489,302 A | 12/1984 | Eventoff |
| 4,490,798 A | 12/1984 | Franks et al. |
| 4,493,704 A | 1/1985 | Beard et al. |
| 4,494,950 A | 1/1985 | Fischell |
| 4,498,843 A | 2/1985 | Schneider et al. |
| 4,512,013 A | 4/1985 | Nash et al. |
| 4,520,706 A | 6/1985 | Deforeit |
| 4,526,574 A | 7/1985 | Pekkarinen |
| 4,529,401 A | 7/1985 | Leslie et al. |
| 4,530,696 A | 7/1985 | Bisera et al. |
| 4,534,756 A | 8/1985 | Nelson |
| 4,542,532 A | 9/1985 | McQuilkin |
| 4,550,731 A | 11/1985 | Batina et al. |
| 4,550,748 A | 11/1985 | Nunez |
| 4,557,725 A | 12/1985 | Heyne et al. |
| 4,559,037 A | 12/1985 | Franetzki et al. |
| 4,559,038 A | 12/1985 | Berg et al. |
| 4,559,044 A | 12/1985 | Robinson et al. |
| 4,561,443 A | 12/1985 | Hogrefe |
| 4,562,751 A | 1/1986 | Nason et al. |
| 4,563,179 A | 1/1986 | Sakai |
| 4,565,542 A | 1/1986 | Berg |
| 4,578,573 A | 3/1986 | Flies et al. |
| 4,596,575 A | 6/1986 | Rosenberg et al. |
| 4,597,754 A | 7/1986 | Thill et al. |
| 4,601,702 A | 7/1986 | Hudson |
| 4,606,353 A | 8/1986 | Timm |
| 4,617,014 A | 10/1986 | Cannon et al. |
| 4,623,331 A | 11/1986 | Cewers et al. |
| 4,624,661 A | 11/1986 | Arimond |
| 4,627,835 A | 12/1986 | Fenton, Jr. |
| 4,627,839 A | 12/1986 | Young |
| 4,649,499 A | 3/1987 | Sutton et al. |
| 4,650,469 A | 3/1987 | Berg et al. |
| 4,652,260 A | 3/1987 | Fenton, Jr. |
| 4,656,603 A | 4/1987 | Dunn |
| 4,658,371 A | 4/1987 | Walsh et al. |
| 4,671,792 A | 6/1987 | Borsanyi |
| 4,676,776 A | 6/1987 | Hawson |
| 4,678,408 A | 7/1987 | Nason et al. |
| 4,681,563 A | 7/1987 | Deckert et al. |
| 4,685,903 A | 8/1987 | Cable et al. |
| 4,690,673 A | 9/1987 | Bloomquist |
| 4,692,147 A | 9/1987 | Duggan |
| 4,696,671 A | 9/1987 | Epstein et al. |
| 4,710,163 A | 12/1987 | Butterfield |
| 4,714,462 A | 12/1987 | DiDomenico |
| 4,722,734 A | 2/1988 | Kollin |
| D294,733 S | 3/1988 | Peterson et al. |
| 4,731,051 A | 3/1988 | Fischell |
| 4,731,058 A | 3/1988 | Doan |
| 4,731,726 A | 3/1988 | Allen |
| 4,739,229 A | 4/1988 | Heiler, Jr. |
| 4,741,732 A | 5/1988 | Crankshaw et al. |
| 4,745,301 A | 5/1988 | Michalchik |
| 4,747,828 A | 5/1988 | Tseo |
| 4,754,401 A | 6/1988 | Kaczynski et al. |
| 4,756,706 A | 7/1988 | Kerns et al. |
| 4,774,029 A | 9/1988 | Poulin |
| 4,775,368 A | 10/1988 | Iwatschenko |
| 4,778,449 A | 10/1988 | Weber et al. |
| 4,785,799 A | 11/1988 | Schoon et al. |
| 4,790,816 A | 12/1988 | Sundblom et al. |
| 4,799,381 A | 1/1989 | Tromp |
| 4,808,161 A | 2/1989 | Karmen |
| 4,808,167 A | 2/1989 | Mann et al. |
| 4,809,697 A | 3/1989 | Causey, III et al. |
| 4,810,243 A | 3/1989 | Howson |
| 4,810,992 A | 3/1989 | Eventoff |
| 4,816,019 A | 3/1989 | Kamen |
| 4,818,186 A | 4/1989 | Pastrone et al. |
| 4,826,810 A | 5/1989 | Aoki |
| 4,832,033 A | 5/1989 | Maher et al. |
| 4,836,752 A | 6/1989 | Burkett |
| 4,838,856 A | 6/1989 | Mulreany et al. |
| 4,838,857 A | 6/1989 | Strowe et al. |
| 4,842,584 A | 6/1989 | Pastrone |
| 4,846,792 A | 7/1989 | Bobo, Jr. et al. |
| 4,847,764 A | 7/1989 | Halvorson |
| 4,847,990 A | 7/1989 | Patrick |
| 4,850,807 A | 7/1989 | Frantz |
| 4,850,972 A | 7/1989 | Schulman et al. |
| 4,852,581 A | 8/1989 | Frank |
| 4,854,324 A | 8/1989 | Hirschman et al. |
| 4,856,339 A | 8/1989 | Williams |
| 4,863,425 A | 9/1989 | Slate et al. |
| 4,869,722 A | 9/1989 | Heyman |
| 4,871,351 A | 10/1989 | Feingold |
| 4,878,896 A | 11/1989 | Garrison et al. |
| 4,882,575 A | 11/1989 | Kawahara |
| 4,889,132 A | 12/1989 | Hutcheson et al. |
| 4,898,578 A | 2/1990 | Rubalcaba, Jr. |
| 4,901,221 A | 2/1990 | Kodosky et al. |
| 4,908,017 A | 3/1990 | Howson et al. |
| 4,914,568 A | 4/1990 | Kodosky et al. |
| 4,918,930 A | 4/1990 | Gaudet et al. |
| 4,919,650 A | 4/1990 | Feingold et al. |
| 4,925,444 A | 5/1990 | Orkin et al. |
| 4,927,411 A | 5/1990 | Pastrone et al. |
| 4,933,873 A | 6/1990 | Kaufman et al. |
| 4,942,514 A | 7/1990 | Miyagaki et al. |

(56) References Cited

U.S. PATENT DOCUMENTS

| | | |
|---|---|---|
| 4,943,279 A | 7/1990 | Samiotes et al. |
| 4,950,235 A | 8/1990 | Slate et al. |
| 4,950,244 A | 8/1990 | Fellingham et al. |
| 4,954,818 A | 9/1990 | Nakane et al. |
| 4,957,690 A | 9/1990 | Fennern |
| 4,961,533 A | 10/1990 | Teller et al. |
| 4,970,664 A | 11/1990 | Kaiser |
| 4,976,151 A | 12/1990 | Morishita |
| 4,978,335 A | 12/1990 | Arthur, III |
| 4,979,940 A | 12/1990 | Bobo, Jr. et al. |
| 4,994,035 A | 2/1991 | Mokros |
| 4,996,511 A | 2/1991 | Ohkawa et al. |
| 5,000,739 A | 3/1991 | Kulisz et al. |
| 5,006,997 A | 4/1991 | Reich |
| 5,009,641 A | 4/1991 | Gorton |
| 5,010,473 A | 4/1991 | Jacobs |
| 5,017,059 A | 5/1991 | Davis |
| 5,032,978 A | 7/1991 | Watson et al. |
| 5,034,004 A | 7/1991 | Crankshaw |
| 5,038,800 A | 8/1991 | Oba |
| 5,041,086 A | 8/1991 | Koenig et al. |
| 5,047,014 A | 9/1991 | Mosebach et al. |
| 5,050,612 A | 9/1991 | Matsumura |
| 5,053,585 A | 10/1991 | Yaniger |
| 5,053,990 A | 10/1991 | Kreifels |
| 5,062,774 A | 11/1991 | Kramer et al. |
| 5,069,668 A | 12/1991 | Boydman |
| 5,074,756 A | 12/1991 | Davis |
| 5,078,682 A | 1/1992 | Miki et al. |
| 5,078,683 A | 1/1992 | Sancoff et al. |
| 5,082,014 A | 1/1992 | Olichney |
| 5,084,828 A | 1/1992 | Kaufman et al. |
| 5,087,245 A | 2/1992 | Doan |
| 5,088,983 A | 2/1992 | Burke |
| 5,096,385 A | 3/1992 | Georgi et al. |
| 5,098,262 A | 3/1992 | Wecker et al. |
| 5,098,409 A | 3/1992 | Stock |
| 5,100,380 A | 3/1992 | Epstein et al. |
| 5,103,211 A | 4/1992 | Daoud et al. |
| 5,104,374 A | 4/1992 | Bishko et al. |
| 5,111,234 A | 5/1992 | Taniguchi et al. |
| 5,115,223 A | 5/1992 | Moody |
| 5,116,312 A | 5/1992 | Blankenship et al. |
| 5,122,820 A | 6/1992 | Pagano et al. |
| 5,124,744 A | 6/1992 | Ogura et al. |
| 5,124,802 A | 6/1992 | Ito et al. |
| 5,131,816 A | 7/1992 | Brown et al. |
| 5,140,862 A | 8/1992 | Pappalardo |
| 5,153,827 A | 10/1992 | Coutre et al. |
| 5,154,700 A | 10/1992 | Danby |
| 5,155,693 A | 10/1992 | Altmayer et al. |
| 5,155,847 A | 10/1992 | Kirouac et al. |
| 5,157,928 A | 10/1992 | Gaudlet et al. |
| 5,168,441 A | 12/1992 | Onarheim et al. |
| 5,172,698 A | 12/1992 | Stanko |
| 5,174,472 A | 12/1992 | Raque et al. |
| 5,176,004 A | 1/1993 | Gaudet |
| 5,181,910 A | 1/1993 | Scanlon |
| 5,190,442 A | 3/1993 | Jorritsma |
| 5,190,522 A | 3/1993 | Wojcicki et al. |
| 5,207,642 A | 5/1993 | Orkin et al. |
| 5,211,626 A | 5/1993 | Frank et al. |
| 5,213,573 A | 5/1993 | Sorich et al. |
| 5,217,355 A | 6/1993 | Hyman et al. |
| 5,219,327 A | 6/1993 | Okada |
| 5,221,268 A | 6/1993 | Barton et al. |
| 5,224,051 A | 6/1993 | Johnson |
| 5,230,623 A | 7/1993 | Guthrie et al. |
| 5,238,001 A | 8/1993 | Gallant et al. |
| 5,241,461 A | 8/1993 | Georges |
| 5,244,461 A | 9/1993 | Derlien |
| 5,244,463 A | 9/1993 | Cordner, Jr. et al. |
| 5,247,434 A | 9/1993 | Peterson et al. |
| 5,256,157 A | 10/1993 | Samiotes et al. |
| 5,265,431 A | 11/1993 | Gaudet et al. |
| 5,267,218 A | 11/1993 | Elbert |
| 5,291,190 A | 3/1994 | Scarola et al. |
| 5,295,062 A | 3/1994 | Fukushima |
| 5,301,301 A | 4/1994 | Kodosky et al. |
| 5,307,262 A | 4/1994 | Ertel |
| 5,307,263 A | 4/1994 | Brown |
| 5,315,530 A | 5/1994 | Gerhardt et al. |
| 5,317,506 A | 5/1994 | Coutre et al. |
| 5,321,601 A | 6/1994 | Riedel et al. |
| 5,338,157 A | 8/1994 | Blomquist |
| 5,339,821 A | 8/1994 | Fujimoto |
| 5,350,411 A | 9/1994 | Ryan et al. |
| 5,353,316 A | 10/1994 | Scarola et al. |
| 5,354,273 A | 10/1994 | Hagen |
| 5,356,378 A | 10/1994 | Doan |
| 5,357,427 A | 10/1994 | Langen et al. |
| 5,363,482 A | 11/1994 | Victor et al. |
| 5,364,346 A | 11/1994 | Schrezenmeir |
| 5,368,562 A | 11/1994 | Blomquist et al. |
| 5,376,070 A | 12/1994 | Purvis et al. |
| 5,383,855 A | 1/1995 | Nicholson et al. |
| 5,386,360 A | 1/1995 | Wilson et al. |
| 5,388,202 A | 2/1995 | Squires et al. |
| 5,389,071 A | 2/1995 | Kawahara et al. |
| 5,389,078 A | 2/1995 | Zalesky et al. |
| 5,395,321 A | 3/1995 | Kawahara et al. |
| 5,400,246 A | 3/1995 | Wilson et al. |
| 5,412,400 A | 5/1995 | Takahara et al. |
| 5,429,602 A | 7/1995 | Hauser |
| 5,431,627 A | 7/1995 | Pastrone et al. |
| 5,432,709 A | 7/1995 | Vollweiler et al. |
| 5,440,585 A | 8/1995 | Patridge, III |
| 5,456,691 A | 10/1995 | Snell |
| 5,478,211 A | 12/1995 | Dominiak et al. |
| 5,479,643 A | 12/1995 | Bhaskar et al. |
| 5,481,250 A | 1/1996 | Hano |
| 5,482,446 A | 1/1996 | Williamson et al. |
| 5,485,408 A | 1/1996 | Blomquist |
| 5,531,697 A | 7/1996 | Olsen et al. |
| 5,531,698 A | 7/1996 | Olsen |
| 5,537,436 A | 7/1996 | Bottoms et al. |
| 5,558,640 A | 9/1996 | Pfeiler et al. |
| 5,569,187 A | 10/1996 | Kaiser |
| 5,573,506 A | 11/1996 | Vasko |
| 5,582,593 A | 12/1996 | Hultman |
| 5,594,786 A | 1/1997 | Chaco et al. |
| 5,598,420 A | 1/1997 | Kaufman |
| 5,616,121 A | 4/1997 | McKay |
| 5,626,144 A | 5/1997 | Tacklind et al. |
| 5,630,710 A | 5/1997 | Tunc et al. |
| 5,643,212 A | 7/1997 | Coutre et al. |
| 5,647,854 A | 7/1997 | Olsen et al. |
| 5,658,250 A | 8/1997 | Blomquist et al. |
| 5,658,252 A | 8/1997 | Johnson |
| 5,660,176 A | 8/1997 | Iliff |
| 5,665,065 A | 9/1997 | Colman et al. |
| 5,669,877 A | 9/1997 | Blomquist |
| 5,681,285 A | 10/1997 | Ford et al. |
| 5,685,844 A | 11/1997 | Marttila |
| 5,687,717 A | 11/1997 | Halpern et al. |
| 5,687,734 A | 11/1997 | Dempsey et al. |
| 5,695,473 A | 12/1997 | Olsen |
| 5,704,366 A | 1/1998 | Tacklind et al. |
| 5,706,458 A | 1/1998 | Koppolu |
| 5,713,856 A | 2/1998 | Eggers et al. |
| 5,717,603 A | 2/1998 | McClendon et al. |
| 5,718,562 A | 2/1998 | Lawless et al. |
| 5,719,761 A | 2/1998 | Gatti et al. |
| 5,729,735 A | 3/1998 | Meyering |
| 5,764,159 A | 6/1998 | Neftel |
| 5,772,635 A | 6/1998 | Dastur et al. |
| 5,781,442 A | 7/1998 | Engleson et al. |
| 5,782,805 A | 7/1998 | Meinzer et al. |
| 5,788,669 A | 8/1998 | Peterson |
| 5,807,336 A | 9/1998 | Russo et al. |
| 5,810,771 A | 9/1998 | Blomquist |
| 5,814,015 A | 9/1998 | Gargano et al. |
| 5,822,715 A | 10/1998 | Worthington et al. |
| 5,857,967 A | 1/1999 | Frid et al. |

(56) References Cited

U.S. PATENT DOCUMENTS

| | | |
|---|---|---|
| 5,861,018 A | 1/1999 | Feierbach |
| 5,868,669 A | 2/1999 | Iliff |
| 5,871,465 A | 2/1999 | Vasko |
| 5,876,370 A | 3/1999 | Blomquist |
| 5,879,163 A | 3/1999 | Brown et al. |
| 5,885,245 A | 3/1999 | Lynch et al. |
| 5,895,371 A | 4/1999 | Levitas et al. |
| 5,897,493 A | 4/1999 | Brown |
| 5,899,855 A | 5/1999 | Brown |
| 5,913,310 A | 6/1999 | Brown |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,935,106 A | 8/1999 | Olsen |
| 5,940,801 A | 8/1999 | Brown |
| 5,950,190 A | 9/1999 | Yeager et al. |
| 5,956,501 A | 9/1999 | Brown |
| 5,960,403 A | 9/1999 | Brown |
| 5,966,691 A | 10/1999 | Kibre et al. |
| 5,997,476 A | 12/1999 | Brown |
| 6,012,034 A | 1/2000 | Hamparian et al. |
| 6,024,539 A | 2/2000 | Blomquist |
| 6,032,119 A | 2/2000 | Brown et al. |
| 6,077,055 A | 6/2000 | Vilks |
| 6,101,478 A | 8/2000 | Brown |
| RE36,871 E | 9/2000 | Epstein et al. |
| 6,241,704 B1 | 6/2001 | Peterson et al. |
| 6,246,992 B1 | 6/2001 | Brown |
| 6,248,057 B1 | 6/2001 | Mavity et al. |
| 6,269,340 B1 | 7/2001 | Ford et al. |
| 6,363,282 B1 | 3/2002 | Nichols et al. |
| 6,406,426 B1 | 6/2002 | Reuss et al. |
| 6,422,057 B1 | 7/2002 | Anderson |
| 6,475,180 B2 | 11/2002 | Peterson et al. |
| 6,551,276 B1 | 4/2003 | Mann et al. |
| 6,554,798 B1 | 4/2003 | Mann et al. |
| 6,558,320 B1 | 5/2003 | Causey, III et al. |
| 6,641,533 B2 | 11/2003 | Causey, III et al. |
| 6,671,563 B1 | 12/2003 | Engelson et al. |
| 6,689,091 B2 | 2/2004 | Bui et al. |
| 6,714,969 B1 | 3/2004 | Klein et al. |
| 6,744,350 B2 | 6/2004 | Blomquist |
| 6,749,586 B2 | 6/2004 | Vasko |
| 6,765,877 B1 | 7/2004 | Foschiano et al. |
| 6,790,198 B1 | 9/2004 | White et al. |
| 6,809,653 B1 | 10/2004 | Mann et al. |
| 6,852,104 B2 | 2/2005 | Blomquist |
| 6,872,200 B2 | 3/2005 | Mann et al. |
| 6,903,743 B2 | 6/2005 | Ng |
| 6,904,434 B1 | 6/2005 | Wallach et al. |
| 6,936,029 B2 | 8/2005 | Mann et al. |
| 6,956,572 B2 | 10/2005 | Zaleski |
| 6,979,326 B2 | 12/2005 | Mann et al. |
| 6,997,920 B2 | 2/2006 | Mann et al. |
| 6,999,854 B2 | 2/2006 | Roth |
| 7,018,361 B2* | 3/2006 | Gillespie et al. ............... 604/151 |
| 7,025,743 B2 | 4/2006 | Mann et al. |
| 7,033,338 B2 | 4/2006 | Vilks et al. |
| 7,036,089 B2 | 4/2006 | Bauer |
| 7,041,082 B2 | 5/2006 | Blomquist et al. |
| 7,042,643 B2 | 5/2006 | Miles |
| 7,098,803 B2 | 8/2006 | Mann et al. |
| 7,103,578 B2* | 9/2006 | Beck et al. ....................... 705/75 |
| 7,109,878 B2 | 9/2006 | Mann et al. |
| 7,300,418 B2 | 11/2007 | Zaleski |
| 7,324,012 B2 | 1/2008 | Mann et al. |
| 7,347,836 B2 | 3/2008 | Peterson |
| D570,363 S | 6/2008 | Ulm et al. |
| 7,384,410 B2 | 6/2008 | Eggers et al. |
| D576,175 S | 9/2008 | Onodera |
| D580,948 S | 11/2008 | Tomizawa et al. |
| D586,351 S | 2/2009 | Gelman et al. |
| D586,357 S | 2/2009 | Jasinski |
| D604,741 S | 11/2009 | DeBelser et al. |
| 7,647,237 B2 | 1/2010 | Malave et al. |
| 7,654,976 B2 | 2/2010 | Peterson et al. |
| 7,689,939 B1 | 3/2010 | Becker |
| 7,708,717 B2 | 5/2010 | Estes et al. |
| 7,789,859 B2 | 9/2010 | Estes et al. |
| 7,794,427 B2 | 9/2010 | Estes et al. |
| 7,835,927 B2 | 11/2010 | Schlotterbeck et al. |
| 8,250,483 B2 | 8/2012 | Blomquist |
| 2001/0031944 A1 | 10/2001 | Peterson et al. |
| 2002/0002326 A1 | 1/2002 | Causey et al. |
| 2002/0029776 A1 | 3/2002 | Blomquist |
| 2002/0065879 A1 | 5/2002 | Ambrose et al. |
| 2002/0107476 A1 | 8/2002 | Mann et al. |
| 2002/0151804 A1 | 10/2002 | O'Mahony et al. |
| 2002/0183693 A1 | 12/2002 | Peterson et al. |
| 2002/0193679 A1 | 12/2002 | Malave et al. |
| 2003/0011646 A1 | 1/2003 | Levine et al. |
| 2003/0060765 A1 | 3/2003 | Campbell et al. |
| 2003/0069650 A1 | 4/2003 | Karmiy et al. |
| 2003/0076792 A1 | 4/2003 | Theimer et al. |
| 2003/0114836 A1 | 6/2003 | Estes et al. |
| 2003/0139701 A1 | 7/2003 | White et al. |
| 2003/0144880 A1 | 7/2003 | Talachian et al. |
| 2003/0145053 A1* | 7/2003 | Bodin et al. ................... 709/205 |
| 2003/0163088 A1 | 8/2003 | Blomquist |
| 2003/0163223 A1 | 8/2003 | Blomquist |
| 2003/0163789 A1 | 8/2003 | Blomquist |
| 2003/0173408 A1 | 9/2003 | Mosher, Jr. et al. |
| 2003/0204413 A1* | 10/2003 | Riff ................................ 705/2 |
| 2003/0204415 A1 | 10/2003 | Knowlton |
| 2003/0204416 A1 | 10/2003 | Radpay et al. |
| 2003/0212364 A1 | 11/2003 | Mann et al. |
| 2003/0212379 A1 | 11/2003 | Bylund et al. |
| 2004/0010425 A1 | 1/2004 | Wilkes et al. |
| 2004/0019607 A1 | 1/2004 | Moubayed et al. |
| 2004/0065321 A1 | 4/2004 | Stenzler |
| 2004/0073095 A1 | 4/2004 | Causey, III et al. |
| 2004/0167465 A1 | 8/2004 | Mihai et al. |
| 2004/0172302 A1* | 9/2004 | Martucci et al. ................ 705/2 |
| 2004/0176984 A1 | 9/2004 | White et al. |
| 2004/0249673 A1* | 12/2004 | Smith ............................. 705/2 |
| 2005/0001797 A1 | 1/2005 | Miller |
| 2005/0030164 A1 | 2/2005 | Blomquist |
| 2005/0055242 A1 | 3/2005 | Bello et al. |
| 2005/0102167 A1 | 5/2005 | Kapoor |
| 2005/0137530 A1 | 6/2005 | Campbell et al. |
| 2005/0143864 A1 | 6/2005 | Blomquist |
| 2005/0144182 A1 | 6/2005 | Boris et al. |
| 2005/0171513 A1 | 8/2005 | Mann et al. |
| 2005/0177395 A1 | 8/2005 | Blomquist |
| 2006/0001550 A1 | 1/2006 | Mann et al. |
| 2006/0026205 A1 | 2/2006 | Butterfield |
| 2006/0041222 A1 | 2/2006 | Dewing et al. |
| 2006/0047538 A1 | 3/2006 | Condurso et al. |
| 2006/0079768 A1 | 4/2006 | Small et al. |
| 2006/0132292 A1 | 6/2006 | Blomquist |
| 2006/0202859 A1 | 9/2006 | Mastrototaro et al. |
| 2006/0229557 A1 | 10/2006 | Fathallah et al. |
| 2007/0156033 A1 | 7/2007 | Causey, III et al. |
| 2007/0213657 A1 | 9/2007 | Jennewine et al. |
| 2007/0255322 A1 | 11/2007 | Gerber et al. |
| 2008/0030369 A1 | 2/2008 | Mann et al. |
| 2008/0033357 A1 | 2/2008 | Mann et al. |
| 2008/0033360 A1 | 2/2008 | Evans et al. |
| 2008/0033361 A1 | 2/2008 | Evans et al. |
| 2008/0033402 A1 | 2/2008 | Blomquist |
| 2008/0033749 A1 | 2/2008 | Blomquist |
| 2008/0034323 A1 | 2/2008 | Blomquist |
| 2008/0065007 A1 | 3/2008 | Peterson et al. |
| 2008/0065016 A1 | 3/2008 | Peterson et al. |
| 2008/0126969 A1 | 5/2008 | Blomquist |
| 2008/0132844 A1 | 6/2008 | Peterson et al. |
| 2008/0300534 A1 | 12/2008 | Blomquist |
| 2009/0177180 A1 | 7/2009 | Rubalcaba et al. |
| 2009/0275886 A1 | 11/2009 | Blomquist et al. |
| 2010/0020064 A1 | 1/2010 | Roosendaal et al. |
| 2011/0060758 A1 | 3/2011 | Schlotterbeck et al. |
| 2011/0282691 A1 | 11/2011 | Coffman et al. |
| 2012/0013625 A1 | 1/2012 | Blomquist et al. |

(56) References Cited

U.S. PATENT DOCUMENTS

| | | | |
|---|---|---|---|
| 2012/0013802 A1 | 1/2012 | Blomquist et al. |
| 2013/0012878 A1 | 1/2013 | Blomquist |
| 2013/0012880 A1 | 1/2013 | Blomquist |
| 2013/0015980 A1 | 1/2013 | Evans et al. |
| 2013/0018315 A1 | 1/2013 | Blomquist |
| 2013/0131630 A1 | 5/2013 | Blomquist |

FOREIGN PATENT DOCUMENTS

| | | |
|---|---|---|
| CH | 665955 | 6/1988 |
| EP | 0069350 | 1/1983 |
| EP | 0078645 | 5/1983 |
| EP | 0183351 | 6/1986 |
| EP | 0188288 | 7/1986 |
| EP | 0221005 | 5/1987 |
| EP | 0233115 | 8/1987 |
| EP | 319272 | 6/1989 |
| EP | 0328162 | 8/1989 |
| EP | 0384155 | 8/1990 |
| EP | 408483 | 1/1991 |
| EP | 0497041 | 8/1992 |
| EP | 503670 | 9/1992 |
| EP | 0371507 | 3/1993 |
| EP | 551088 | 7/1993 |
| EP | 0806738 | 12/1997 |
| EP | 0952541 | 10/1999 |
| EP | 1587017 | 10/2005 |
| EP | 1647291 | 4/2006 |
| FR | 2603488 | 3/1988 |
| FR | 2675288 | 10/1992 |
| GB | 2039083 | 7/1980 |
| GB | 2262452 | 6/1993 |
| GB | 2312055 | 10/1997 |
| JP | 409192218 | 7/1997 |
| JP | 10143573 | 5/1998 |
| JP | H10143573 | 5/1998 |
| JP | 11502132 | 2/1999 |
| JP | 11505352 | 5/1999 |
| JP | 2002291706 | 10/2002 |
| WO | WO8703814 | 7/1987 |
| WO | WO8707161 | 12/1987 |
| WO | WO91/16609 | 10/1991 |
| WO | WO92/08647 | 5/1992 |
| WO | WO92/15439 | 9/1992 |
| WO | WO94/05355 | 3/1994 |
| WO | WO94/08647 | 4/1994 |
| WO | WO 8403218 | 8/1994 |
| WO | WO95/02426 | 1/1995 |
| WO | WO95/25893 | 9/1995 |
| WO | WO95/28190 | 10/1995 |
| WO | WO96/03168 | 2/1996 |
| WO | WO9613790 | 5/1996 |
| WO | WO96/20745 | 7/1996 |
| WO | WO96/36389 | 11/1996 |
| WO | WO97/15227 | 5/1997 |
| WO | WO97/25083 | 7/1997 |
| WO | WO98/20439 | 5/1998 |
| WO | WO98/24358 | 6/1998 |
| WO | WO98/42407 | 10/1998 |
| WO | WO98/59487 | 12/1998 |
| WO | WO99/08183 | 2/1999 |
| WO | WO99/10801 | 3/1999 |
| WO | WO99/18532 | 4/1999 |
| WO | WO99/22236 | 5/1999 |
| WO | WO9932031 | 7/1999 |
| WO | WO0003344 | 1/2000 |
| WO | WO0018449 | 4/2000 |
| WO | WO 00/48112 | 8/2000 |
| WO | WO0045696 | 8/2000 |
| WO | WO 0152727 | 7/2001 |
| WO | WO02/11049 | 2/2002 |
| WO | WO03/053503 | 7/2003 |
| WO | WO03/094075 | 11/2003 |
| WO | WO 2005/056083 | 6/2005 |
| WO | WO 2005/083619 | 9/2005 |
| WO | WO2006/023636 | 3/2006 |
| WO | WO 2006/073400 | 7/2006 |
| WO | WO2008/019013 | 2/2008 |
| WO | WO2008/019014 | 2/2008 |
| WO | WO2008/019015 | 2/2008 |
| WO | WO2008016621 | 2/2008 |
| WO | WO2008/048587 | 4/2008 |
| WO | WO2008/019016 | 11/2008 |
| WO | WO2009/135108 | 11/2009 |

OTHER PUBLICATIONS

Steinfeld, E., "Internet-appliance Technology Automates Test Equipment," *EDN*, www.ednmag.com, pp. 157-169 (Oct. 12, 2000).

Steinfeld, E., "Is Embedded Going Net-Crazy? A Response,"*TechOnLine*, 1 page (Mar. 29, 2001).

Application and File History for U.S. Appl. No. 29/306,071, filed Apr. 1, 2008, inventor DeBleser et al.

Application and File History for U.S. Appl. No. 10/087,449, filed Feb. 28, 2002, inventor Blomquist.

Application and File History for U.S. Appl. No. 11/702,925, filed Feb. 25, 2007, inventors Evans et al.

Application and File History for U.S. Appl. No. 11/066,425, filed Feb. 22, 2005, inventor Blomquist.

Application and File History for U.S. Appl. No. 11/003,147, filed Dec. 3, 2004, inventor Blomquist.

Application and File History for U.S. Appl. No. 11/499,255, filed Aug. 3, 2006, inventor Blomquist.

Application and File History for U.S. Appl. No. 11/702,922, filed Feb. 5, 2007, inventors Evan et al.

Application and File History for U.S. Appl. No. 11/499,893, filed Aug. 3, 2006, inventor Blomquist.

Application and File History for U.S. Appl. No. 11/499,248, filed Aug. 3, 2006, inventor Blomquist.

Application and File History for U.S. Appl. No. 11/499,240, filed Aug. 3, 2006, inventor Blomquist.

Application and File History for U.S. Appl. No. 11/981,788, filed Oct. 31, 2007, inventor Peterson et al.

Application and File History for U.S. Appl. No. 11/981,248, filed Oct. 31, 2007, inventor Peterson et al.

Application and File History for U.S. Appl. No. 10/087,205, filed Feb. 28, 2002, inventor Blomquist.

Application and File History for U.S. Appl. No. 12/114,033, filed May 2, 2008, inventors Blomquist et al.

Application and File History for U.S. Appl. No. 07/942,288, filed Sep. 9, 1992, inventor Blomquist.

Application and File History for U.S. Appl. No. 08/090,738, filed Jul. 13, 1993, inventor Blomquist See Application and File History for U.S. Appl. No. 08/555,304, filed Nov. 8, 1995, inventor Blomquist.

Application and File History for U.S. Appl. No. 08/206,737, filed Mar. 7, 1994, inventor Blomquist.

Application and File History for U.S. Appl. No. 08/276,025, filed Jul. 15, 1994, inventor Blomquist.

Application and File History for U.S. Appl. No. 08/540,960, filed Oct. 11, 1995, inventor Blomquist See Application and File History for U.S. Appl. No. 08/782,486, filed Jan. 10, 1997, inventor Peterson.

Application and File History for U.S. Appl. No. 08/555,304, filed Nov. 8, 1995, inventor Blomquist.

Application and File History for U.S. Appl. No. 08/561,809, filed Nov. 22, 1995, inventor Peterson.

Application and File History for U.S. Appl. No. 08/586,952, filed Jan. 16, 1996, inventor Blomquist See Application and File History for U.S. Appl. No. 08/782,486, filed Jan. 10, 1997, inventor Peterson.

Application and File History for U.S. Appl. No. 08/782,486, filed Jan. 10, 1997, inventor Peterson.

Application and File History for U.S. Appl. No. 08/800,477, filed Feb. 14, 1997 inventor Blomquist.

Application and File History for U.S. Appl. No. 08/868,913, filed Jun. 4, 1997, inventor Blomquist.

Application and File History for U.S. Appl. No. 08/934,875, filed Sep. 22, 1997, inventor Blomquist.

Application and File History for U.S. Appl. No. 08/978,779, filed Nov. 26, 1997, inventor Blomquist.

(56) References Cited

OTHER PUBLICATIONS

Application and File History for U.S. Appl. No. 09/324,305, filed Jun. 2, 1999, inventor Peterson.
Application and File History for U.S. Appl. No. 09/795,266, filed Feb. 27, 2001, inventor Peterson.
Application and File History for U.S. Appl. No. 10/068,291, filed Feb. 5, 2002, inventor Peterson.
Application and File History for U.S. Appl. No. 11/981,229, filed Oct. 31, 2007, inventor Peterson.
Application and File History for U.S. Appl. No. 09/421,751, filed Oct. 20, 1999, inventor Blomquist.
DVD—University of Maryland at College Park MD. Human-Computer Interaction Laboratory, Apr. 1991.
DVD—University of Maryland at College Park MD. Human-Computer Interaction Laboratory, Apr. 1992.
Invitation to Pay Additional Fees with Partial International Search for International Application No. PCT/US2007/017133 mailed Feb. 27, 2008.
International Search Report for International Application No. PCT/US94/07582 dated Oct. 28, 1994.
Notification of Reasons for Refusal for Japanese Patent Application No. 2006-542752 dated Jun. 23, 2010.
International Search Report for International Application No. PCT/US2007/017122 dated Feb. 19, 2008.
Written Opinion for International Application No. PCT/US2007/017122 dated Feb. 19, 2008.
International Search Report for International Application No. PCT/US2005/005829 dated Nov. 10, 2005.
Written Opinion for International Application No. PCT/US2005/005829 dated Nov. 10, 2005.
International Search Report for International Application No. PCT/US2004/040397 dated Feb. 7, 2006.
Written Opinion for International Application No. PCT/US2004/040397 dated Feb. 7, 2006.
International Search Report for International Application No. PCT/US2007/017138 dated Nov. 20, 2007.
Written Opinion for International Application No. PCT/US2007/017138 dated Nov. 20, 2007.
International Search Report for International Application No. PCT/US2007/017123 dated Jan. 25, 2008.
Written Opinion for International Application No. PCT/US2007/017123 dated Jan. 25, 2008.
International Search Report for International Application No. PCT/US2007/017120 dated Jan. 25, 2008.
Written Opinion for International Application No. PCT/US2007/017120 dated Jan. 25, 2008.
European Office Action for European Application No. 05713999 dated Oct. 30, 2009.
International Search Report for International Application No. PCT/US2007/017133 dated May 8, 2008.
Written Opinion for International Application No. PCT/US2007/017133 dated May 8, 2008.
International Search Report for International Application No. PCT/US2007/022051 dated Mar. 7, 2008.
Written Opinion for International Application No. PCT/US2007/022051 dated Mar. 7, 2008.
Declaration of non-establishment of ISR for International Application No. PCT/US2009/042494 dated Jan. 5, 2010.
Written Opinion for International Application No. PCT/US2009/042494 dated Jan. 5, 2010.
European Office Action for European Application No. 07797060 dated Jul. 3, 2009.
European Office Action for European Application No. 07797060 dated Feb. 9, 2010.
European Office Action for European Application No. 07797060 dated Dec. 8, 2010.
Australian Office Action for Application No. 2004296794 dated Dec. 3, 2009.
Notification of Reasons for Refusal for Japanese Patent Application No. 2006-554321 dispatch date Apr. 19, 2010.
Decision of Refusal for Japanese Application No. 2006-554321 dispatch date Apr. 18, 2011.
Examiner's first report on patent application No. 2005216321 by Smiths Medical ASD, Inc dated Nov. 26, 2009.
Examiner's report No. 3 on patent application No. 2005216321 by Smiths Medical ASD Inc. dated Apr. 20, 2011, Australian Government IP.
Notification of Reasons for Refusal for Japanese Application No. 2006-542752 dispatch date Jun. 28, 2010.
Examiner's first report on patent application No. 2004296794 by Smiths Medical ASD, Inc. dated Dec. 3, 2009. Australian Government IP.
Examiner's report No. 2 on patent application No. 2005216321 by Smiths Medical ASD, Inc. dated Jan. 7, 2011. Australian Government IP.
Decision of Refusal for Japanese Application No. 2006-542752 dispatch date Jul. 4, 2011.
Application and File History for U.S. Appl. No. 09/421,751, filed Oct. 20, 1999, inventorBlomquist.
Examiner's first report on patent application No. 2007282071 dated Jul. 11, 2011.
Devices for Insulin Administration , Jean-Louis Selam, MD and M. Arthur Charles, MD, PhD., Diabetes Care, vol. 13, No. 9, Sep. 1990. pp. 955-979.
A Semi-closed loop computer-assisted insulin infusion system, Donald J. Chisholm, Edward W. Kraegen, David J. Bell and David R. Chipps, The Medical Journal of Australia, Dec. 8-22, 1984. pp. 13-17.
Hypertensive Crisis Managed by Computer-Controlled Infusion of Sodium Nitroprusside; A Model for the Closed-Loop Administration of Short-Acting Vasoactive Agents. Jeremy J. Hammond, Walter M. Kirkdendall, Richard V. Calfee, Comupters and Biomedical Research, vol. 12, pp. 97-108, 1979.
Computerized Continuous Infusion of Intravenous Anesthetic Drugs During Pediatric Cardiac Surgery; Kern FH, Ungerleider RM, Jacobs JR, Boyd JL 3rd, Reyes JG, Goodman D. Greeley WJ; Department of Anesthesiology, Duke Heart Center, Duke University Medical Center, Durham, North Carolina, Anesth Analg. Apr. 1991; 72(4): 487-92.
Use of a Microprocessor in the Control of Malignant Hypertension with Sodium Nitroprusside, Jackson RV, Love JB, Parkin WG, Wahlquist ML, Williams NS, Aust N Z J Med. Aug. 1977; 7(4):414-7.
Effective Control of Blood Pressure by Computerized Infusion of Sodium Nitroprusside, R.V. Calfee, J.J. Hammond, W.M. Kirkendall, Clinical Research, vol. 25, 1977.
Automated Patient Care Following Cardiac Surgery. Nicholas T. Kouchoukos; Louis B. Sheppard; John W. Kirklin, Cardiovascular Clinics, Bol. 3, pp. 110-120, 1971.
A Simulation Study on a Self-Tuning Portable Controller of Blood Glucose. Brunetti P, Cobelli C, Cruciani P, Fabietti PG, Filippucci F, Santeusanio F, Sarti E. Medical Pathology Institute, Bioengineering Laboratory. University of Perugia, Italy. Int. J. ArtifOrgans. Jan. 1993; 16(1):51-7.
A Semi-Closed Loop Computer-Assisted Insulin Infusion System. Hospital use for Control of Diabetes in Patients, Chisholm DJ, Kraegan EW, Bell DJ, Chipps DR, Med J. Aust. Dec. 8-22, 1984;141(12-13):784-9.
Patient-controlled Portable Insulin Infusion Pump in Diabetes, Jergen Bojsen, Thorsten Deckert, Klaus Kelendorf, and Birthe Lerup, Diabetes vol. 28 Nov. 1979. Cover page and pp. 974-979.
Block Medical: Growing awith Home Infusion Therapy, In Vivio, The Business and Medicine Report, Apr. 1991, 3 pages.
Abbot Literature, 37 pages, as submitted Jun. 29, 1988 in U.S. Appl. No. 08/868,913.
Baxter Literature for MultiPlex™ Series 100 Fluid Management System, 4 pages, as submitted Jun. 29, 1988 in U.S. Appl. No. 08/868,913.
Baxter Literature for Flo-Guard® 6201 Volumetric Infusion Pump, Copyright 1992, 2 pages.
Greg Sancoff. San Diego Executive, "A Better Mousetrap," Sep. 1989, 4 pages.
Blade-Citizen, "Entrepeneur takes Aim at Home Health Care Market," Dec. 31, 1989, 2 pages.

(56) References Cited

OTHER PUBLICATIONS

"Product Overview, Verifuse Ambulatory Infusion Pump." Block Medical Inc, dated Sep. 1990, 4 pages.
Peter Lord et al., "MinMed Technologies Programmable Implantable Infusion System,"pp. 66-91, from Annals of the New York Academy of Sciences, Neurilogical Applications of Implanted Drug Pumps, Copyright 1988.
Dertouzos, M., "Communications, Computers & Net-works," Scietific American Sep. 1991, pp. 62-69.
Dehne, T., "PC-Based Data Acquisition and Intrumentation," Analytical Chemistry, vol. 62, No. 9, May 1, 1990. pp. 565A, 566A, 568A, 570A, 571A, 572A.
"ally™ Ambulatory Frug Infusion System", Q-Life Systems Inc., 3 pages, as submitted Jun. 29, 1988 in U.S. Appl. No. 08/868,913.
Fundamentals of Interactive Computer Graphics, Foley et al., Mar. 1993, pp. 10, 11, 29-35.
IMED Status Infusion Management System literature, 6 pages, as submitted Jun. 29, 1988 in U.S. Appl. No. 08/868,913.
Linkens et al., Computer Control Systems and Pharmacological Drug Administration: A Survey, Journal of Medical Engineering & Technology, vol. 14, No. 2, Mar./Apr. 1990, pp. 41-54.
McCarthy, LH, Software Simulates Instrumentation Systems, Design News, May 21, 1990, pp. 72-73.
National Instruments Document entitled "Scientific Data Analysis," 16 pages, as submitted Jun. 29, 1988 in U.S. Appl. No. 08/868,913.
National Instruments Instrumentation Newsletter, Aug. 1990, 20 pages. vol. 2, No. 3.
National Instruments Instrumentation Newsletter, Feb. 1991, 20 pages. vol. 3, No. 1.
National Instruments Instrumentation Newsletter, May 1990, 18 pages. vol. 2, No. 2.
National Instruments Instrumentation Newsletter, Nov. 1990, 16 pages. vol. 2, No. 4.
National Instruments Lab Windows 2.0 materials, 6 pages, as submitted Jun. 29, 1988 in U.S. Appl. No. 08/868,913.
National Instruments Lab Windows 1.2 materials dated Oct. 1989, 5 pages.
Bedder, M. et al., "Cost Analysis of Two Implantable Narcotic Delivery Systems," Journal of Pain and Symptom Management. vol. 6, No. 6, Aug. 1991. pp. 368-373.
Principles and Guidelines in Software User Interface Design, Deborah J. Mayhew, Chapter 9 Dialog Sryles: Direct Manipulation, copyright 1992, 17 pages.
Advertisement from HERCO, Are Control Rooms Obsolete? Dated Mar. 1971, 1 page and Mar. 1972, 1 page.
Electronics Feb. 1990 article entitled "Who Will Dominate the Desktop in the '90's?", 3 pages.
The Orange County Register No. 21, 1991 article entitled "Portable TV frees patients," 1 page.
Article by McMorris et al., "Are Process Control Rooms Obsolete?", Control Engineering dated Jul. 1971, pp. 42-47.
LabVIEW® User Manual, Jan. 1990 Edition, cover page and pp. 2-1 through 2-36.
National Instruments' 1991 catalog entitled "IEEE-488 and VXIbus Control, Data Acquisition, and Analysis," cover page and pp. 1-1 through 1-13, 1-38, 4-68 and 4-69.
Abbot Laboratories Blue Line System Life Care® Model 4 Series System brochure, copyright 1990, 16 pages.
Operator's Manual for a CADD-Micro™ Ambulatroy Infusion Pump Model 5400, front cover and pp. ii-vi, pp. 1-55 and two back cover pages, copyright 1990.
Instruction Manual entitled "Quick Start for Speakerphone XT SVD", copyright 1996.
Bio Tek Instruments, Inc. Products Catalog. 32 pages. Apr. 1992.
Intel® document entitled, 28F001BX-T/28F001BX-B 1M(128Kx8) CMOS Flash Memory, dated Mar. 1991, 28 pages.
Intel® document entitled, 28F008SA8MBIT (1MBITx) Flashtile™ Memory dated Mar. 1992, 28 pages.
Lahti W. et al., "Byte", pp. 311-318, Nov. 1990. "Store Data in a Flash".
"A Programable Infusion Pump Controller," 30th Annual Conference on Engineering in Medicine and Biology, Nov. 5-9, 1977 in Los Angeles, California, 11 pages.
"IV700 Service Manual." Valleylab, Inc. Boulder Colorado; Sep. 1988.
Designing the User Interface, Ben Shneiderman, Chapter 5 Direct Manipulation, Oct. 1993, 56 pages.
Operator's Manual for a CADD-Micro® Ambulatory Infusion Pump Model 5900, front cover and pp. ii-vi and 1-84, copyright 1993.
Provider® One Instruction Manual, Pancretec, Inc. as submitted on May 18, 1998 in U.S. Appl. No. 08/782,486.
Sheppard, L.C., Computerbased Clinical Systems: Automation and Intergration, 39th Annual Conference on Engineering in Medicine and Biology, Baltimore, Maryland, Sep. 13-16, 1986, pp. 73-75.
Wilson R., "Integrated Circuits" of Computer Design, pp. 26-27, Jun. 1, 1989.
Zales, S et al., Microprocessors and Microsystems vol. 14, No. 8, pp. 543-549, Oct. 1990.
Intravenous propofol anaesthesia using a computerized infustion system, M. White and G.N.C. Kenny, Anaesthesia, 1990, vol. 45, pp. 204-209.
Health Devices, ECRI A Nonprofit Agency, vol. 17 No. 12, Dec. 1988.
Health Devices, ECRI A Nonprofit Agency, vol. 19 Nos. 3-4, Mar.-Apr. 1989.
Operator's Manual, Gemini® PC-1 Volumetric Infusion Pump/Controller imed® Aug. 16, 1990.
Model 929 Computer Controlled Volumetric Infusion Pump Operating Instructions imed® as submitted Feb. 28, 2008 in U.S. Appl. No. 11/981,788.
Pain Control Devices Gaining Acceptance, Will Expand—Analgesic Delivery Devices—Industry Overview, http://www.findarticles.com/articles/mi_m3498/is_n5_v55/ai_12257770, Sep. 29, 2004.
A Standard Microcomputer Linked to a Volume-Controlled Infusion Pump for Patient-Controlled Analgesia Research, Journal of Medical Engineering and Technology, G.W.A. Gillies, G.N.C. Kenny and C.S. McArdle, vol. 10, No. 2, Mar./Apr. 1986. pp. 55-57.
The P1073 Medical Information Bus, David F. Franklin and David V. Ostler (Oct. 1989).
IMED 980 Volumetric Infusion Pump Operator's Manual. 1992.
Improving Acute Care Use of Medical Device Data, Robert J. Kennelly, Chair, IEEE 1073 "Standard for Medical Device Communications" Committee, Eden Shores Consulting. 1992.
Health Devices, ECRI A Nonprofit Agency, Sep. 1991, vol. 20, No. 9.
Medtronic MiniMed Paradigm Link Owner's Guide, BD Logic, 2003.
M68HC11 E Series, HCMOS Microcontroller Unit, Motorola, Inc. 1993, 1996.
Health Devices, ECRI A Nonprofit Agency, Dec. 1989, vol. 18 No. 12.
Health Devices, ECRI A Nonprofit Agency, Dec. 1991, vol. 20 No. 12.
510 (k) Registration Documents for Registration of K87022 and K871728 (1987).
510 (k) Registration Documents for Registration of K863997 (1986).
Complaint for Patent Infringement (Exhibits 1-3); C.A. No. 03-776, *Medtronic Minimed, Inc.* v. *Deltec Inc., and Smiths Medical Ltd.* Aug. 5, 2003.
First Amended Complaint for Patent Infringement (Exhibits 1-3); C.A. No. 03-776, *Medtronic Minimed, Inc.* v. *Deltec Inc. Smiths Group North America Inc. and Smiths Medical Ltd.* Nov. 3, 2003.
Answer and Counterclaims of Smiths Medical Md. Inc. (Exhibits 1-5); C.A. 03-776, *Medtronic Minimed, Inc.* v. *Deltec Inc., Smiths Group North America, Inc. and Smiths Group Pic.* Nov. 17, 2003.
Joint Claim Construction Statement (Exhibits 1-2); C.A. No. 03-776, *Medtronic Minimed, Inc.* v. *Smiths Medical Md, Inc.* Certificate of service Feb. 4, 2005.
Expert Response of Anthony Storace on behalf of Defendant Counterclaimant Smiths Medical Md., Inc. to the Expert Report Submitted by jack Goldberg on behlaf of Plaintiff Medtronic Minimed (Exhibits B-J); C.A. No. 03-776, *Medtronic Minimed Inc.* v. *Smiths Medical Md, Inc.* Jan. 14, 2005.

(56) References Cited

OTHER PUBLICATIONS

Medtronic Minimed's Reply Brief in Support of it's Motion for Summary Judgment of Non-Infringement of Claims 6 and 11 of Smiths '704 Patent (Exhibits A-B), *Medtroni Minimed Inc.* v. *Smith Medical Md, Inc.* Mar. 4, 2005.
Medtronic Minimed's Reply Brief in Support of its Motion for Sumamry Judgment of Invalidilty of Claims 6 and 11 of Smiths '704 Patent (Exhibits A-B); C.A. No. 03-776, *Medtronic Minimed Inc.* v. *Smiths Medical MD, Inc.* Mar. 4, 2005.
Defendant Smiths Medical Md. Inc. S. Answering Brief Responding to Medtronic Minimed Inc.'S Claim Contruction Brief for U.S. Patent No. 6,241,704, C.A. No. 03-776, *Medtronic Minimed Inc.* V. *Smiths Medical Md. Inc.* Feb. 25, 2005.
Declaration of Anthony C. Roth in Support of Defendant-Counterclaim Plantiff Smiths Medical Md, Inc. 'S Response Brief to Medtronic Minimed, Inc.'S Claim Construction Brief of U.S. Patent No. 6,241,704 (Exhibits A-H); C.A. No. 03-776, *Medtronic Minimed Inc.* v. *Smith Medical Md, Inc.* Feb. 25, 2005.
Defendant Smiths Medical Md, Inc. 'S Brief in Opposition to Medtronic Minimed, Inc 'S Motion for Summary Judgment of Invalidity of Claims 6 and 11 of Smiths Medical Inc. 'S U.S. Patent No. 6,241,704; C.A. No. 03-776, *Medtronic Minimed, Inc.* v. *Smiths Medical Md. Inc.* Feb. 28, 2005.
Declaration of Anthony C. Roth in Support of Defendant-Counterclaim Plaintiff Smiths Medical Md, Inc. 'S Brief in Opposition of Medtronic Minimed Inc. 'S Motion for Summary Judgment of invalidity of claims 6 and 11 of Smiths Medical Inc. 'S U.S. Patent 6,241,704 (Exhibits 1-7); C,A, No. 003-7769, *Medtronic Minimed Inc.* v. *Smiths Medical Md. Inc.* Feb. 28, 2005.
Expert Report of Jack Goldberg on behalf of Plaintiff Medtronic Minimed Pursuant to Fed R. Civ. P. 26(A)(2) (Exhibits A-F); C.A. No. 03-776, *Medtronic Minimed Inc.* v. *Smiths Medical Md. Inc.* Executed Dec. 15, 2004.
Opening Brief in Support of Defendant Smiths Medical, Inc.'S Propsed Claim Contructions for U.S. Patent Nos. 6,241,704; 6,554,065 and 6,554,798 (Exhibits 1-20); C.A. No. 03-776, *Medtronic Minimed, Inc.* v. *Smiths Medical Md, Inc.* Feb. 4, 2005.
Memorandum Opinion: C.A. No. 03-776, *Medtronic Minimed, Inc.* v. *Smiths Medical Md. Inc.* Jun. 1, 2005.
Order: C.A. No. 03-776; *Medtronic Minimed Inc.* v. *Smiths Medical Md. Inc.* Jun. 1, 2005.
Memorandum Opinion (Summary Judgment of Infringement of U.S. Patent Nos. 5,665,065 and 6,554,798), C.A. No. 03-776, *Medtronic Minimed Inc.* v. *Smiths Medical Md. Inc.* Jun. 16, 2005.
Examiner's first report No. 4 on Australian patent application No. 2005216321 dated Aug. 25, 2011.
Examiner's first report on Australian patent application No. 2007282069 dated Jul. 11, 2011.
Examiner's first report on Australian patent application No. 2007281512 dated Jul. 4, 2011.
Australian Office Action dated May 10, 2012 for Australian Application No. 2007282068.
Notification of Reasons for Refusal for Japanese Application No. 2006-542752 dated Jun. 23, 2010.
Decision of Refusal for Japanese Application No. 2006542752 dated Jun. 27, 2011.
Notification of Reasons for Refusal for Japanese Application No. 2011-240566 dated Feb. 15, 2013.
Canadian OA for Canadian Application No. 2548256 dated Oct. 23, 2012.
European Communication for European Application No. 04812832.6-1225 dated Oct. 30, 2012.
User Information CADD-Diplomat™ PC Communications System, 7 pages. Nov. 1999. Exhibit D.
CADD-Diplomat™ PC Communications System Prodcut Brochure, 4 pages. Jun. 1998. Exhibit C.
Screen Prints from CADD-Diplomat™ PC Communications System CD-ROM 15 pages. Mar. 1998. Exhibit B.
User Information CADD-Diplomat™ PC Communications System, 6 pages. Dated Mar. 1998. Exhibit A.
Anonymous, "Acute HealthCare Solutions", Dosewatch to use Multum's MediSource. PR Newswire. Feb. 26, 1998, 3 pages.
"Giesen.," Credit Card Terminals Are Growing Up. vol. 4, No. 2., p. 96-100. May 1991. ISSN: 0896-9329.
Canadian OA for Canadian Application No. 2552580 dated Jul. 15, 2013.
Notification of Reasons for Refusal for Japanese Patent Application No. 2011177880 date of dispatch Feb. 12, 2013.
Application and File History for U.S. Appl. No. 13/619,740, filed Sep. 14, 2012, inventor Blomquist.
Application and File History for U.S. Appl. No. 13/619,647, filed Sep. 14, 2012, inventor Blomquist.
Application and File History for U.S. Appl. No. 09/920,467, filed Aug. 1, 2001 inventor Blomquist.
European Communication for European Application No. 090088220-1952 dated Nov. 15, 2013.
Canadian Office Action from Canadian Application No. 2,552,580 dated Sep. 5, 2012.
Configuring a Network Bridge, Windows server. (2003).
Jovanov, et al., "Patient Monitoring Using Person Area Networks of Wireless Intelligent Sensors", Biomedical Sciences Instrumentation. vol. 37 pp. 373-378. (2001).
www.activejump.com published on Dec. 12, 2002 as per wayback engine.
Japanese Decision of Refusal for Japanese Application No. 2011-240566 drafting date Dec. 18, 2013.
Canadian Office Action from Canadian Application No. 2,548,256 dated Apr. 8, 2014.
Australian Examiner's Report No. 3 for Australian Application No. 2011218603 dated Feb. 4, 2014.
Notification of Reasons for Refusal for Japanese Application No. 2011177880 dated Jan 6, 2014. English Translation is provided.
Australian Notice of Acceptance for Australian Application No. 2012216290 dated Apr. 3, 2014.
European Communication for European Application No. 05713999.0-1951 dated May 27, 2014.
Japanese Decision of Refusal from Japanese Application No. 2011-177880 drafting date Sep. 29, 2014. English translation provided.

\* cited by examiner

SERVER FOR MEDICAL DEVICE

REFERENCE TO CO-PENDING APPLICATION(S)

The present application is a continuation of U.S. Provisional Patent Application Ser. No. 60/547,642, filed Feb. 23, 2004, the entire disclosure of which is hereby incorporated by reference.

TECHNICAL FIELD

The present invention relates to medical devices, and more particularly, a server for medical devices such as pumps.

BACKGROUND

Medical pumps are an important part of providing care to a patient. They are used for a variety of different therapies such as pain relief, nutrition, chemotherapy, and insulin. Each one of these therapies typically requires a different program for controlling operation of the pump. Additionally, each program typically requires different operating parameters for each patient depending on a variety of factors such as the substance prescribed for delivery, the prescribed dosage, and physical attributes of the patient.

Additionally, medical clinics, hospitals, or other facilities need to manage all of their medical pumps. Managing the pumps requires updating programs, loading the appropriate program into the pump depending on the prescribed therapy, loading and tracking operating parameters into the pump, and tracking performance of the pump.

All of these issues present a tremendous amount of information related to the patient and the pump that needs to be tracked, managed, and coordinated. Examples of such information includes patient records, standing orders, prescriptions, and the like. These issues also present a great deal of functionality that must be executed, managed, and coordinated. Examples include programming pumps, tracking pump inventory, downloading pump software and upgrades, monitoring and relaying alarm conditions, and tracking pump history logs.

Additionally, when an institution has a variety of different networked devices through which a caregiver would like to communicate with the pumps, each one needs to be individually programmed to communicate with the pumps. This programming drives up the cost and time required to network programmable devices and pumps. The cost and required time is even greater when the institution has a variety of different pumps and medical devices because the networked devices would require separate programming to communicate with each different make and model of medical pump or other medical device.

SUMMARY

In general terms, the present invention is directed to communicating with a medical device such as a pump.

One aspect of the present invention is a server for communicating with a medical device. The server comprises a web browser process for communicating with a remote device and a pump interface process for communicating with a medical device.

Another aspect of the present invention is a medical device. The medical device comprises memory configured to store data and a programmable circuit in electrical communication with the memory. The programmable circuit is programmed with a web server for communicating data with a remote device.

Another aspect of the invention is a server for communicating with a medical device. The server comprises memory for storing data and a programmable circuit in electrical communication with the memory. The programmable circuit programmed with an interface for communicating with a medical device.

One aspect of the invention set forth herein is a pump server that provides all communication with a set of medical devices such as a medical pump. Other networked devices that exchange information (e.g., commands, instructions, or other data) with the networked medical devices communicate that information through the pump server.

Another aspect of the invention is the use of a web server to communicate with a medical device such as a medical pump. The use of a web server in this manner may permit a remote device to communicate with a medical device such as a medical pump without the use of a pump server and without the need for a special program or other interface loaded on the remote device.

DETAILED DESCRIPTION

Figure 1:
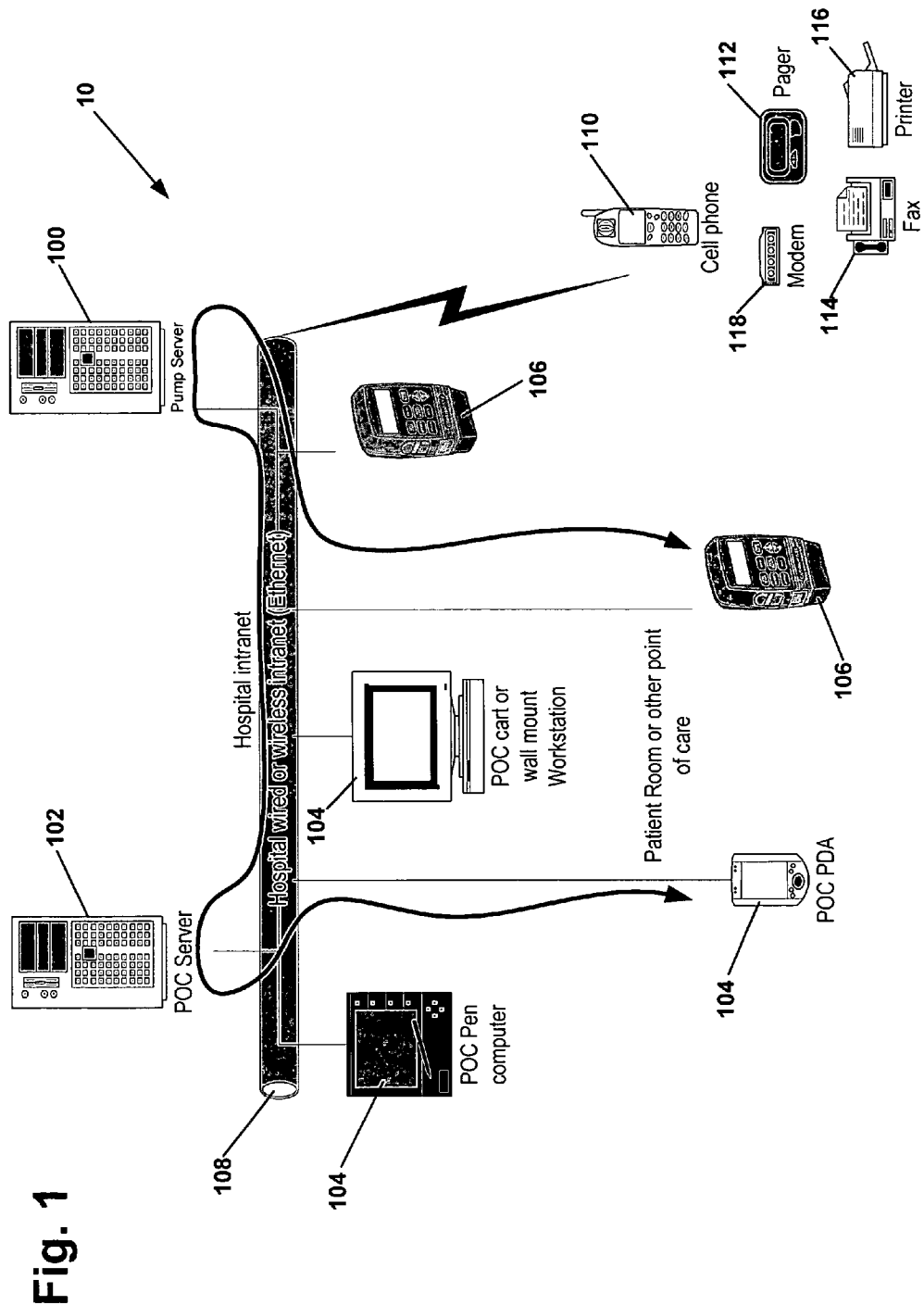
FIG. 1 illustrates a networked system that includes a medical device server and embodying the present invention.

Various embodiments of the present invention will be described in detail with reference to the drawings, wherein like reference numerals represent like parts and assemblies throughout the several views. Reference to various embodiments does not limit the scope of the invention, which is limited only by the scope of the claims attached hereto. Additionally, any examples set forth in this specification are not intended to be limiting and merely set forth some of the many possible embodiments for the claimed invention. There are alternative embodiments for all of the structures and methods disclosed herein regardless of whether specific alternatives are set forth.

Referring to FIG. 1, one possible embodiment of a pump server system 10 includes a pump server 100, a point of care (POC) server 102, one or more programmable devices 104, and one or more medical pumps 106. The pump server 100 and the POC server 102 are connected to a computer network 108. Additionally, the pump server system 10 includes communication/output devices such as a mobile phone 110, a pager 112, a fax machine 114, a printer 116, and a modem 118. The server 100 is called a "pump server" as an exemplary embodiment for purposes of explanation. The server 100 can be used to communicate with any type of medical device, including medical devices other than medical pumps.

The network 108 can be any appropriate network capable of transporting data from one device to another, including a wired network such as an Ethernet network, a wireless network such as an 802.11a/b/g or other wifi network. Additionally, the network 108 can be any type of data network such as an internal network, the Internet, or an Intranet.

The pump server 100 and the POC server 102 divide and coordinate tasks for managing information, executing various functions, and communicating with various devices within the pump server system 10. The pump server 100 and the POC server 102 can be any programmable device that stores information and performs critical functions for the storage of that information. In various embodiments, the server also might be programmed to execute various functions related to the operation and monitoring of medical pumps 106. A structure that includes a separate pump server 100 and POC server 102 has several advantages. For example, the medical pumps 106 need to be programmed and otherwise configured to interface with only one device—the pump server 100. Another advantage for institutions that utilize medical pumps 106 from different manufactures or even different pumps from the same manufacturer is that various components of networked hardware do not need to be programmed with all of the different pumps—only the pump server 100 needs to be programmed to talk directly with the medical pumps 106. As a result, it is simpler and more cost effective for a caregiver institution to add and remove various medical pumps 106 from its inventory of equipment.

The pump server 100 communicates directly with the pumps 106 and with the POC server 102. The POC server then communicates with all of the other devices. In this exemplary embodiment, the POC server 102 instructs the pump server 100 to retrieve data from any selected medical pump 106 in communication with the network 108; instructs the pump server 100 to send data to any selected medical pump 106 in communication with the network 108; and requests data from the pump server 100 regarding any selected medical pump 106 regardless of whether the selected medical pump 106 is in communication with the network 108.

Although the exemplary embodiment illustrates an architecture in which the programmable devices 104 communicate through a POC server 102, other embodiments are possible. In various embodiments, programmable devices 104 and systems other than the POC server 102 might communicate directly with the pump server 100. Examples include programmable devices in a biomedical engineering (biomed) department of a caregiver institution. Such biomed programmable devices might communicate with the medical pumps 106 directly through the pump server 100 for a variety of different reasons such as tracking pump performance, running pump diagnostics, or downloading pump error logs. Other systems or other departments within an institution might communicate directly with the pump server 100 as well. Other examples include a caregiver institution's pain service, which monitors and treats patient's pain, pharmacies, and computerized physician order entry (CPOE) systems, which physicians use to enter prescriptions.

The pump server stores a variety of data, executes a variety of functions, and communicates directly with the medical pumps 106 and the POC server 102 through the network 108. In an exemplary embodiment, the pump server 100 requests and receives information (e.g., I.D. of current program and version loaded in the medical pump 106, history log, alarm status, battery state, and biomed status such as odometers, time until next scheduled maintenance, etc.) from the medical pumps 106 on the network 108; receives unsolicited messages (e.g., alarms, manual pump program changes, pre-programmed periodic updates, etc.) from the medical pumps 106; maintains a database of information retrieved from or sent to the medical pumps 106; provides a web browser interface to the medical pumps 106, which allows a caregiver to perform a variety of tasks from networked programmable devices 104 including remotely viewing the I.D. and version of the program currently loaded on a medical pumps 106, viewing the status of a medical pumps 106, and in one possible embodiment, allowing a caregiver to change various programming parameters such as setup and titration; providing pump alert functionality such as sending emails, pages, or notices to client applications upon the occurrence of certain pump events (e.g., alarms, programming changes, patient tampering, ratio of dose attempts to doses given too high indicating the patient pain is not adequately controlled, and programming that exceeds soft limits programmed into the medical pump 106); sending messages to the display on the medical pumps 106 (e.g., when alarms are acknowledged, display message to patient stating that nurse is on the way); sending voice messages to the medical pumps 106 (e.g., when alarms are acknowledged, tell patient that nurse is on the way); sending messages (e.g., medical pump 106 needs reservoir changed at approximately 8:00 pm) to the printer 116 or the fax 114 at a nursing station; providing information (e.g., electronic copy of manuals, troubleshooting guides, patient guides, etc.) about the medical pumps 106 to a caregiver using programmable devices 104; verifying the software revision for programs loaded on the medical pumps 106 and downloading new or updated software to the medical pumps 106; and controlling pump and document results during biomed testing processes.

In another possible embodiment, the pump server 100 implements Standing Order protocols. An example of implementing Standing Order protocols is described in U.S. Provisional Patent Application Ser. No. 60/526,810, which was filed on Dec. 4, 2003 and entitled "PROGRAMMING MEDICAL PUMPS WITH ELECTRONIC STANDING ORDER TEMPLATE," the disclosure of which is hereby incorporated by reference. In this embodiment, the pump server 100 enables the creation, storage, and management of a database of Standing Orders; processes requests from the medical pumps 106 to send it an index of standing order protocols or specific standing orders; sends Standard Orders-based protocols to the medical pumps 106; and sends updated library of Standing Orders-based protocols to the medical pumps 106;

Additionally, the pump server 100 is programmed to provide notification to a caregiver about when it is time to check on a patient. For example, the pump server 100 might generate a notification to check on a patient or check fluid levels every two hours. Notification can be through any suitable means such as a pop-up window on a programmable device, a pager, a cell phone, a printer, a fax, or the like.

In yet another possible embodiment, when a medical pump 106 is programmed, the pump server 100 disables the medical pump 106 until its programmed parameters (e.g., delivery protocol) is reviewed by a caregiver at the point of care. In one possible programming procedure as illustrated in FIG. 8, when a medical pump 106 is programmed, the pump server 100 sends a disable signal or command to the medical pump 104 at operation 140. Pumping operation of the medical pump is then disabled. The caregiver programs the medical pump 106 while it is disabled at operation 142. After programming is complete, the caregiver reviews the programmed settings at operation 144. In one possible embodiment, the medical pump 106 automatically indexes through the programmed settings. In another possible embodiment, the caregiver must press a button or activate a menu item to acknowledge that the programmed settings were reviewed and accurate. After the programmed settings are reviewed, the medical pump 106 sends a signal to the pump server 100 at operation 146, and the pump server 100 replies to the medical pump 106 with an enable signal on command at operation 148. The medical pump can then pump fluid as programmed.

The pump server 100 can have different locations depending on the desired embodiment. In the exemplary embodiment, the pump server 100 is located at the caregiver's facilities. In another possible embodiment, the pump server 100 is located at a third party, such as the pump manufacturer or other third-party administrator.

The medical pump 106 can be any medical pump configured for infusing a fluid into a patient. It includes a data port configured for communicating with the network 108. Examples of possible data ports for the medical pump 106 includes a wireless data card for transmitting according to the 802.11 a/b/g, Bluetooth, or other appropriate wireless networking protocol, USB data ports, firewire data ports, RS-232 data ports, an infrared data port, a modem, or any other data port capable of communicating with the network 108 or directly with the pump server 100. In the operation of one possible embodiment, the medical pump 106 talks directly and only to the pump server 100 via the network 108. Accordingly, the medical pump 106 requires no knowledge or programming for interfacing with and talking to the POC server 102 or other devices in the pump server system 10.

In one possible embodiment, the programmable devices 104 communicate with the POC server 102 via the network 108 and do not communicate directly with the pump server 100 of the medical pumps 106. The programmable devices can include any type of computing platform capable of data input and interfacing with the network 108. In various embodiments, the programmable devices 104 are mounted in a convenient location such as a hospital room, nurse's station, or other location convenient for the caregiver. Additionally, another embodiment includes a desk-top computer on a cart that can be conveniently rolled from one location to another. Examples of various programmable devices 104 include a pen-based computer such as a Tablet PC, a lap-top computer, a desk-top computer, or a hand-held computing platform such as a personal digital assistant (PDA). Additionally, one possible embodiment of the PDA can include a bar code reader or radio frequency ID (RFID) reader capable of scanning a barcode or RFID tag, respectively, on a medical pump 106 and then communicating this information to the POC server 102.

Figure 2:
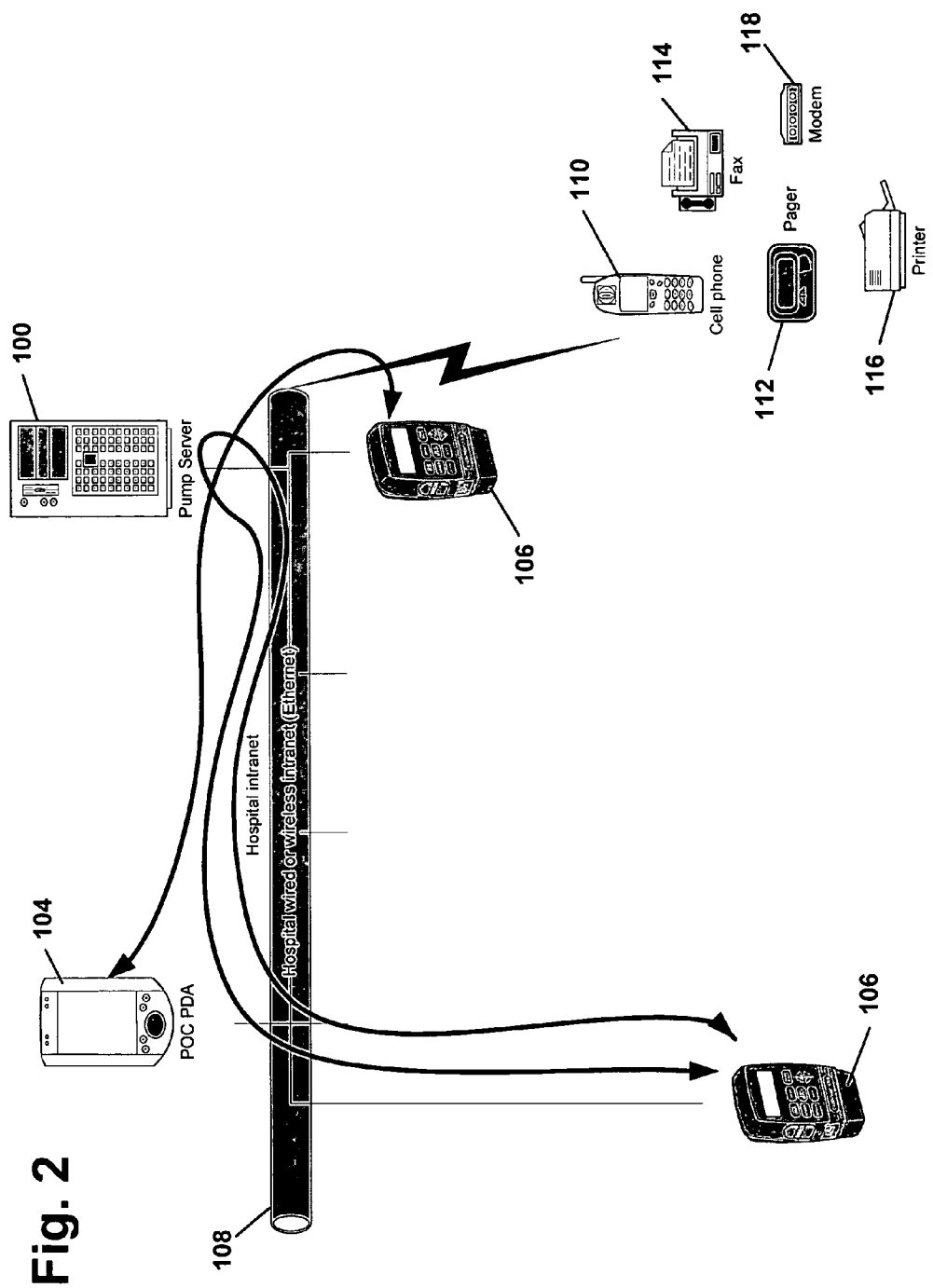
FIG. 2 illustrates an alternative embodiment of the networked system illustrated in FIG. 1.

FIG. 2 illustrates an alternative embodiment in which the programmable devices 104 and the communication/output devices such as a mobile phone 110, a pager 112, a fax machine 114, a printer 116, and a modem 118 communicate directly with the pump server 100 without a POC server 102.

Figure 3:
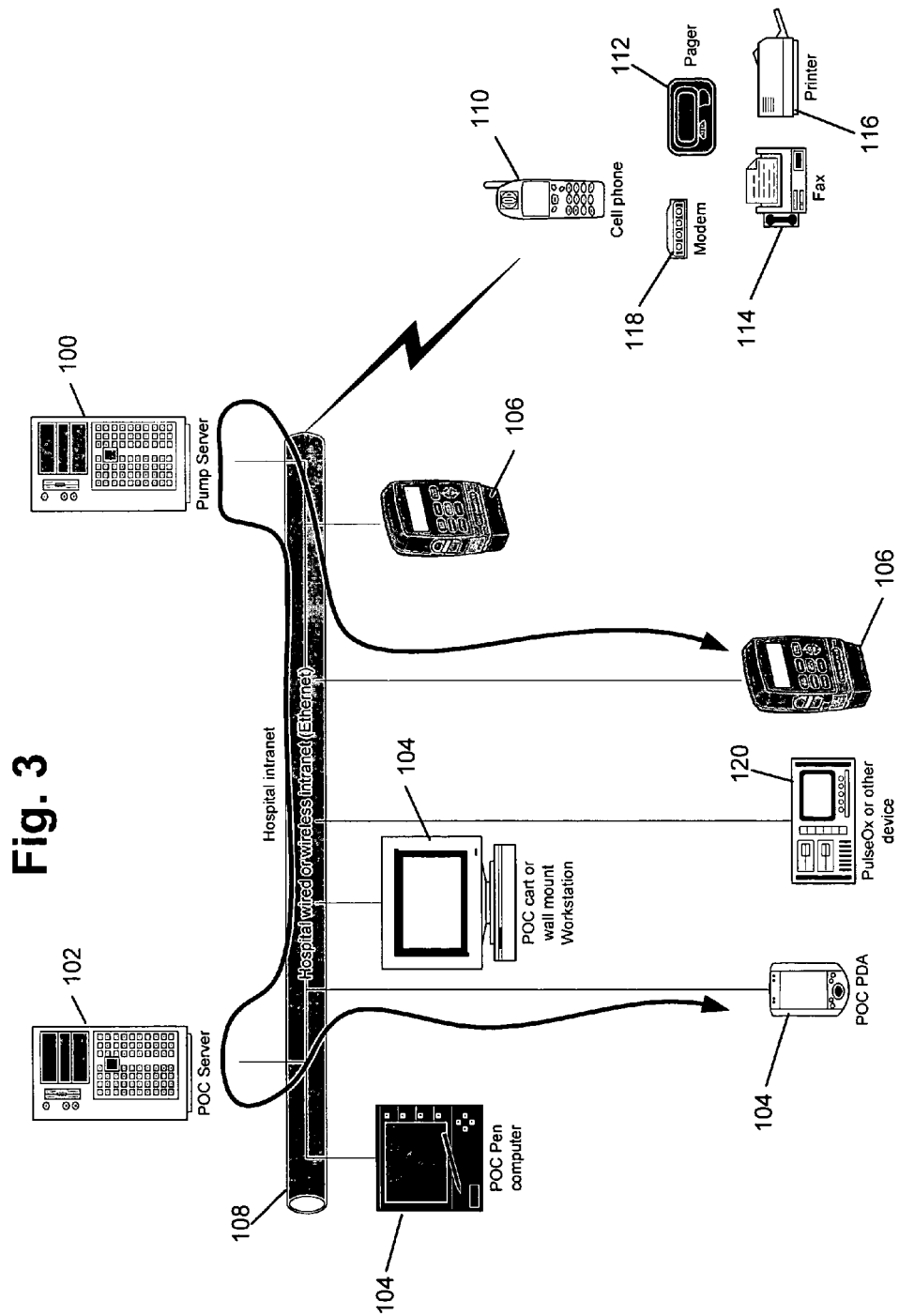
FIG. 3 illustrates an alternative embodiment of the networked system illustrated in FIG. 1.

FIG. 3 illustrates another possible embodiment that includes additional point of care medical devices 120 such as a pulse oximeter. As with the medical pumps 106, the other medical devices 120 communicate directly with the pump server 100 over the network 108 rather than communicating with other networked devices. In this embodiment, the pump server 100 is programmed to selectively associate various medical devices 120 and/or medical pumps 106 using a set of programmed rules that a caregiver may define. For example, the pump server 100 can be programmed to start or stop operation of a medical pump 106 based on data received from another medical device 120 (e.g., if respiration drops below a predefined limit, the pump server 100 instructs the medical pump 106 to stop pumping and generates an alarm). The pump server 100 also selectively provides a virtual connection between the various medical pumps 106 and medical devices. As a result, the medical devices 120 and medical pumps 106 do not need to be programmed to talk directly with each other. Again, because each medical device does not need to be individually programmed, this functionality makes it easier and less costly to add various devices to the inventory of equipment. As with medical pumps 106, the pump server 100 is programmed to generate and/or communicate various alerts for the medical devices 120 via pages, e-mail, faxes, printouts, voice messages, etc.

Figure 4:
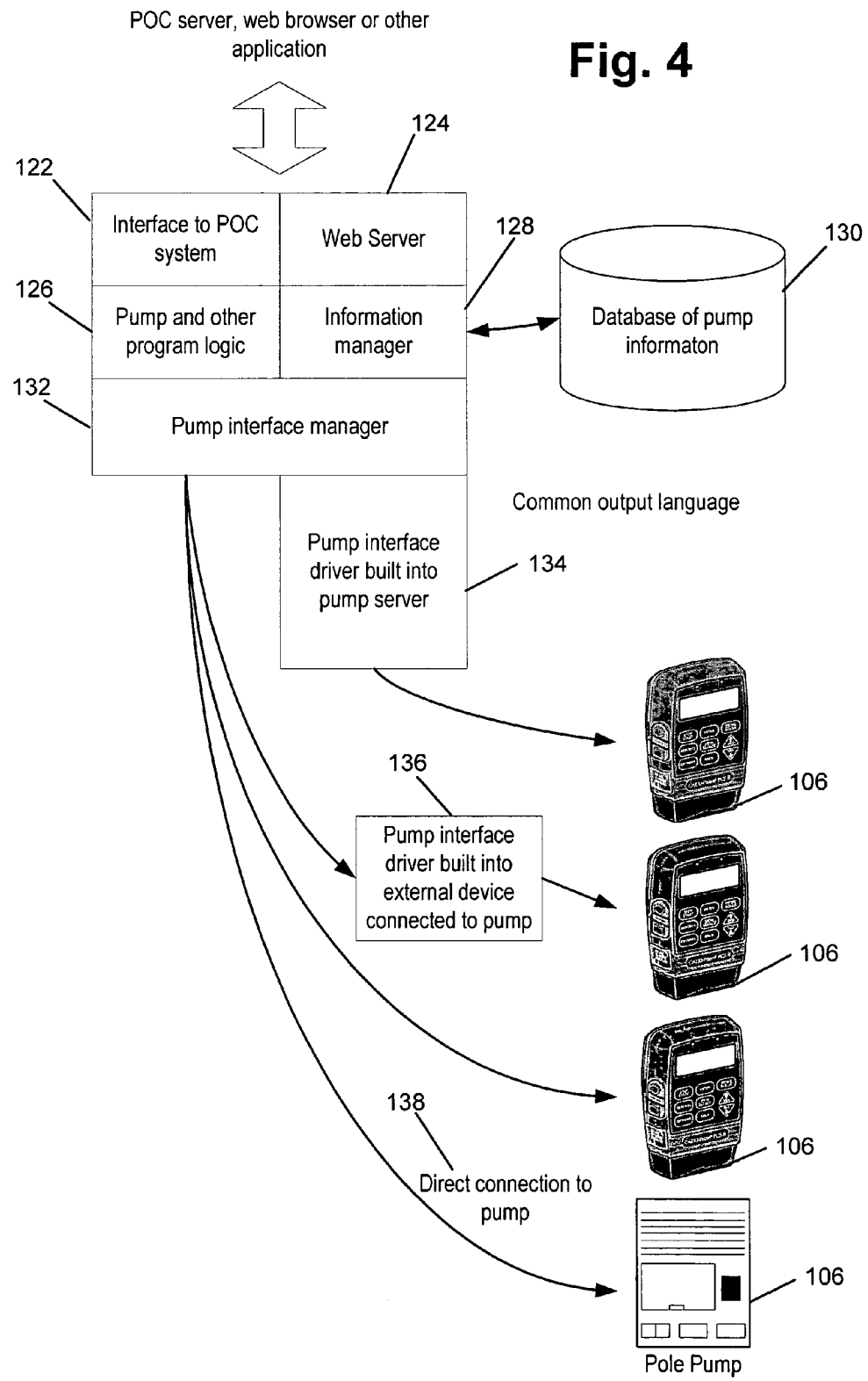
FIG. 4 illustrates software architecture for the pump server illustrated in FIG. 1.

FIG. 4 illustrates one possible embodiment of the architecture for the pump server 100. In this embodiment, the pump server 100 includes an interface 122 for communicating with the POC server 102 and a Web server 124, which allows other devices such as the programmable devices 104 to remotely interface with the medical pumps 106 or other medical devices 120. The web server 124 allows the other devices to communicate with the pump server 100 using standard text files without the need of loading special software such as interfaces, communications software or other programs into the remote or other devices. A remote device includes any device that is a separate and distinct device from the medical device 120. Examples of standard text files include files formed according to a markup language such as a hypertext markup language (HTML), standard generalized markup language (SGML), and extensible markup language (XML).

The pump server 100 is also programmed with various code and logic 126 for executing various tasks and functions described herein and an information manager 128 for storing and retrieving pump information in a database 130. A pump interface manager 132 provides an interface for the medical pumps 106. In various embodiments, the pump interface driver 134 for the medical pump 106 itself is programmed into the pump server 100, or in an alternative embodiment, the pump interface driver 136 is either programmed in the medical pump 106 itself or in a programmable module attached to the medical pump 106. Additionally, one possible embodiment allows the medical pump 106 to have a direct connection 138 to the pump server 100.

Figure 5:
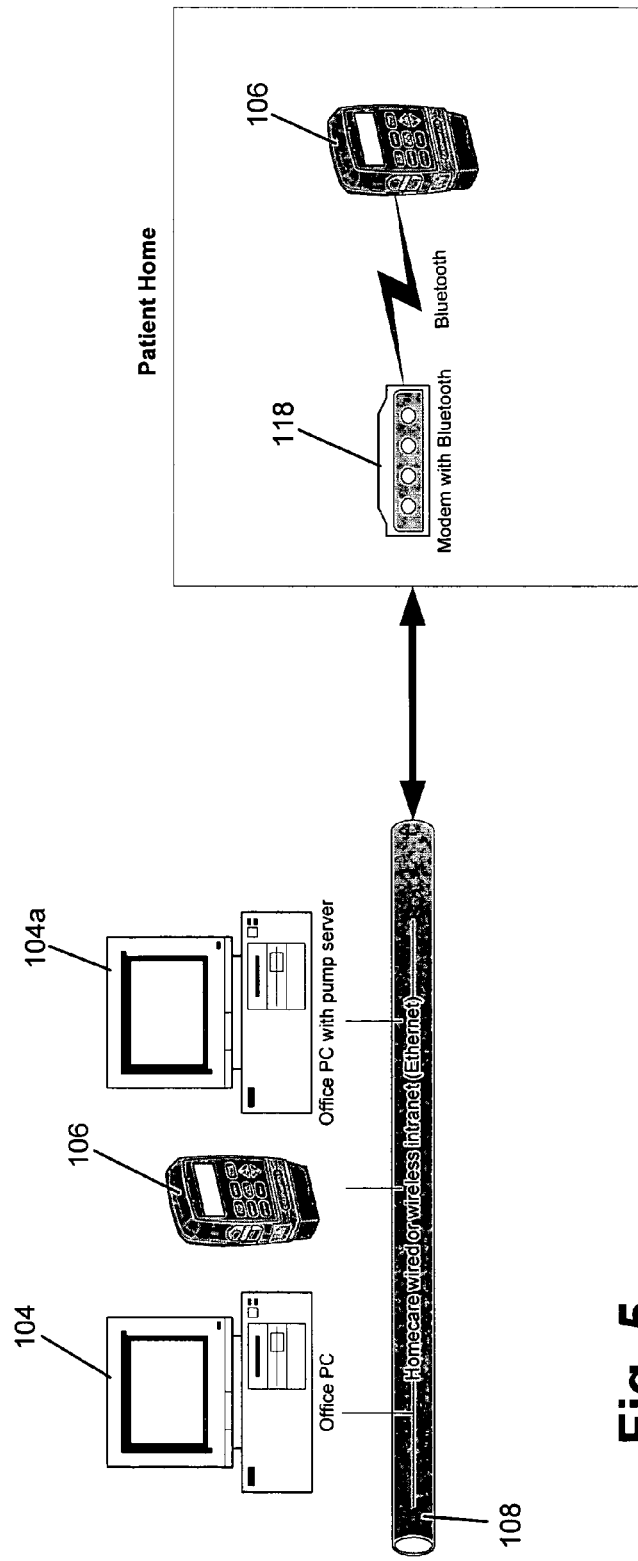
FIG. 5 illustrates an alternative embodiment of the networked system illustrated in FIG. 1.

FIG. 5 illustrates a possible embodiment in which a programmable device 104a is programmed to function as a pump server. In this embodiment, the programmable device 104a performs the same functions as the pump server 100 as described herein. Additionally, the programmable device 104a can request and receive information from medical pumps 106 that are remotely located at a location such as a patient home or a medical pump 106 that is not otherwise provided with a direct network connection. The connection between the programmable device 104a and the medical pump 106 is through a dialup connection using a modem 118. The medical pump 106 can connect to the modem 118 through a wired or wireless connection such as a connection operating according to the Bluetooth protocol. Either the programmable device 104a or the medical pump 106 can initiate a data connection between the two. Accordingly, the programmable device 104a can request and receive information about any medical pump 106 or other medical device 120 that is not on the network 108 as otherwise described herein. Additionally, the medical pump 106 or other medical device 120 can transmit to the programmable device 104a unsolicited messages such as alarms, manual pump changes, preprogrammed period updates, etc.

Figure 6:
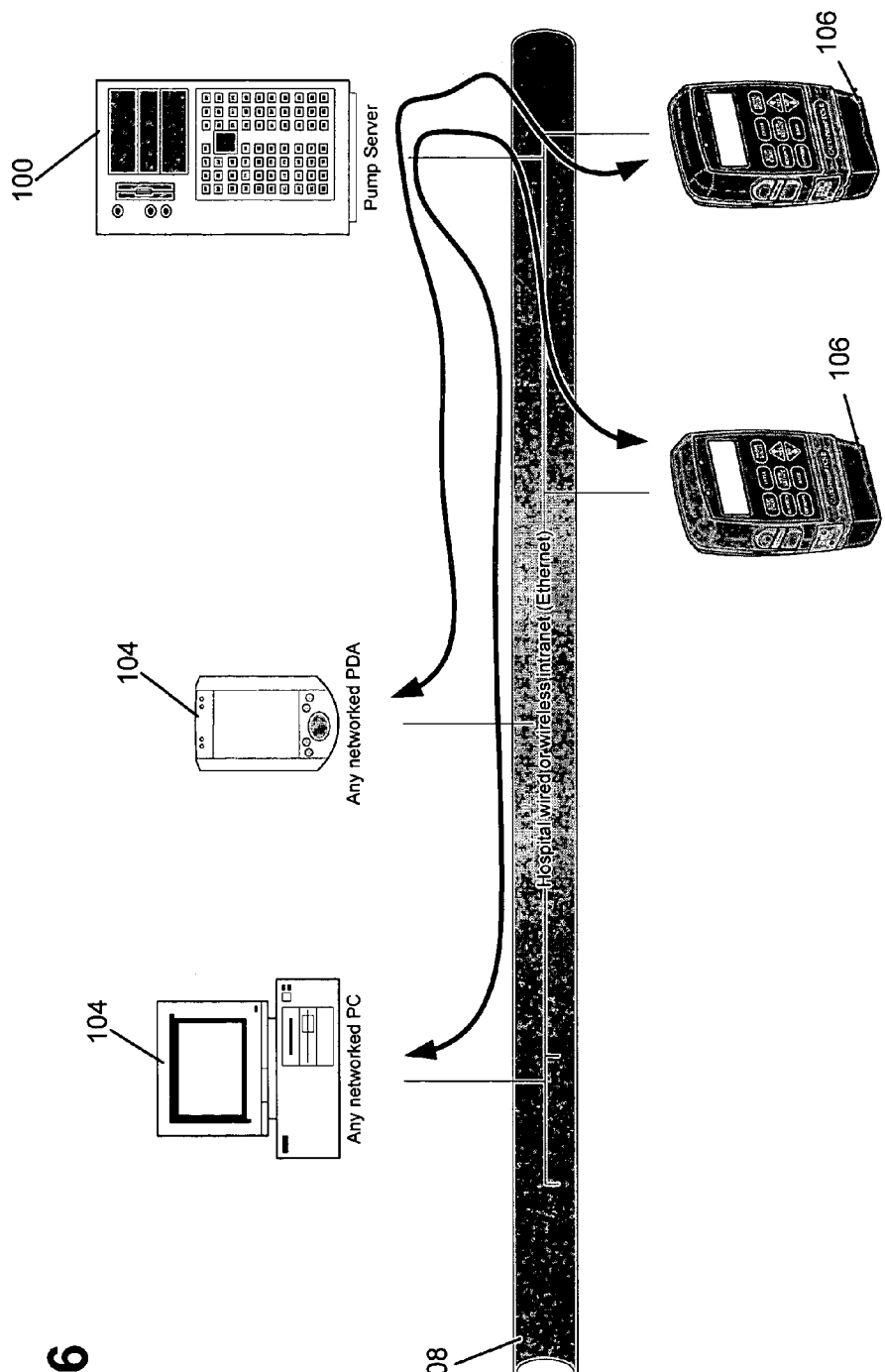
FIG. 6 illustrates an alternative embodiment of the networked system illustrated in FIG. 1.

FIG. 6 illustrates the possible embodiment in which the programmable devices 104 communicate directly with the pump server 100 through a web server programmed in the pump server. In this embodiment, any networked programmable device 104 with a web browser can communicate with the medical pump 106 or any other medical device. An advantage of this embodiment is that a caregiver can connect to the medical pump with wireless and remote devices to check the status of the medical pump 106 or other any medical device when not physically with the patient or located at a site where there is a networked programmable device 104. Another advantage is that the programmable devices 104 do not need to be individually programmed to communicate with the pump server 100.

Figure 7:
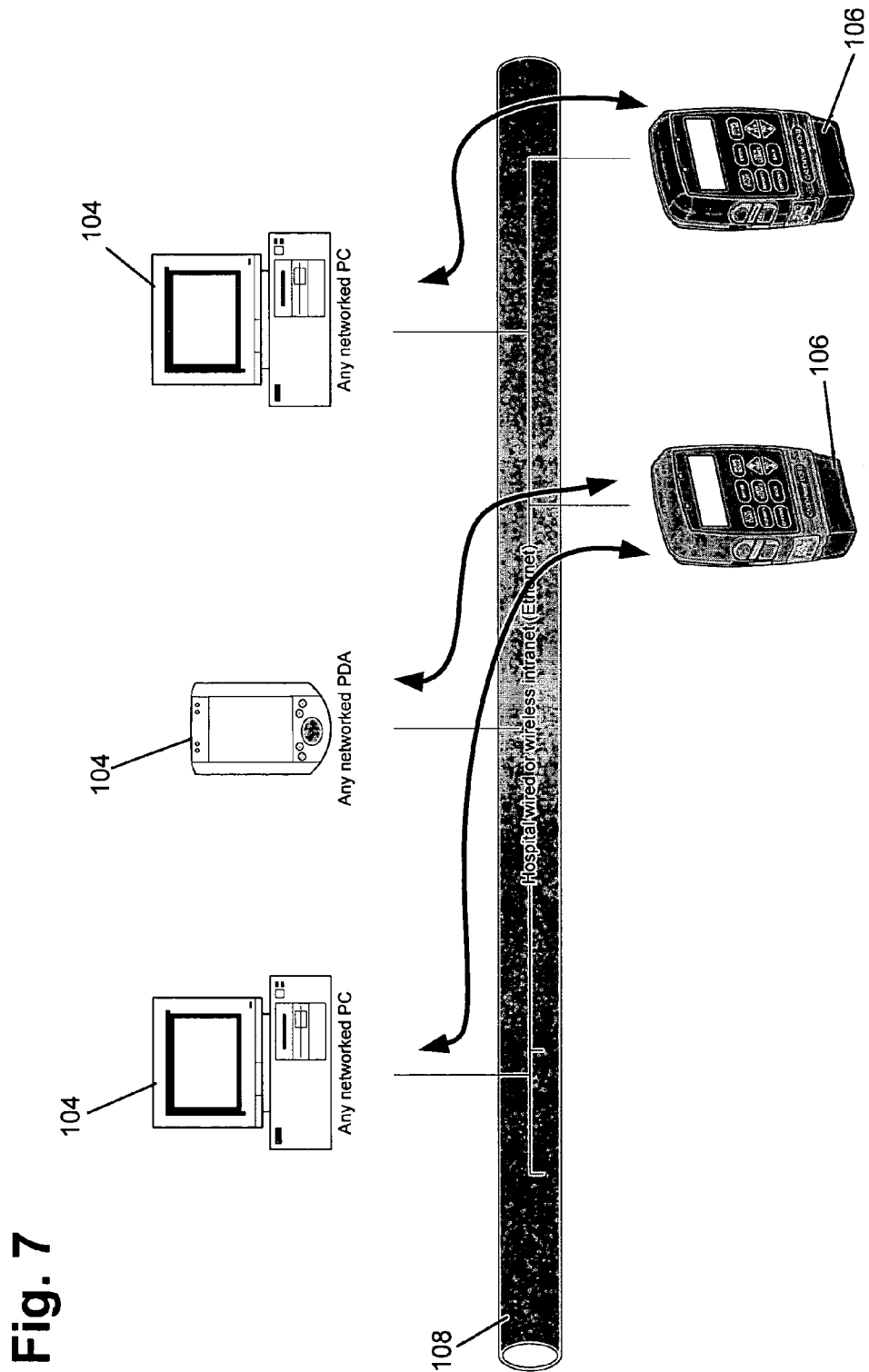
FIG. 7 illustrates an alternative embodiment of the networked system illustrated in FIG. 1.

FIG. 7 illustrates another possible embodiment in which the pump 106 or other medical device 120 is itself programmed with a web server, which allows the medical device 120 to communicate with the pump server 100 or directly with other or remote devices using standard text files without the need of loading special software such as interfaces, communications software, or other programs into the other devices. Again, examples of standard text files include files formed according to a markup language such as a hypertext markup language (HTML), standard generalized markup language (SGML), and eXtensible markup language (XML).

An advantage of this embodiment is that a caregiver can connect to the medical pump with wireless and remote devices, from any distance, to check the status of the medical pump 106 or other medical device 120 when not physically with the patient or located at a site where there is a networked programmable device 104. Additionally, two programmable devices 104 can be simultaneously connected to the same medical pump 106 or other medical device 120 for training and troubleshooting. Additionally, a medical pump 106 or other programmable device 120 can be utilized without a display and without a keyboard. Another advantage is that because the web server provides an interface using a standardized protocol to communicate information such as serving up documents, files, scripts, and other information, no further program or control application need be written for the programmable devices 104.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

The claimed invention is:

1. A medical pump comprising:
   memory configured to store data; and
   a programmable circuit in electrical communication with the memory, the programmable circuit comprising a web server, wherein data communicated between the medical pump and a remote device comprises data related to operation of the medical pump, wherein the web server includes a standardized interface adapted to communicate with a plurality of remote devices, wherein at least two of the plurality of remote devices can be connected to the interface at the same time, and wherein at least one of the plurality of remote devices comprises a medical device server, the medical device server configured to transmit and receive data related to operation of the medical pump,
   wherein the medical pump is operably coupleable to a patient and configured to provide a therapy to the patient.

2. The medical pump of claim 1 wherein the programmable circuit is further programmed to communicate text files with the remote device.

3. The medical pump of claim 2 wherein the text files are coded with a markup language.

4. The medical pump of claim 3 wherein the text files include text having a format selected from the group consisting of: hypertext markup language (HTML), standard generalized markup language (SGML), and eXtensible markup language (XML).

5. The medical pump of claim 1 wherein the medical pump is a pole-mounted pump.

6. A system for communicating with at least two medical devices pumps, the system comprising:
   a first medical pump operably coupleable to a patient and configured to provide a therapy to the patient;
   a second medical pump operably coupleable to the patient or a second patient and configured to provide a therapy to the patient or the second patient;
   at least one remote device configured to transmit and receive data related to operation of the first and second medical pumps;
   a first server comprising:
      memory for storing data, and
      a programmable circuit in electrical communication with the memory, the programmable circuit programmed with a first interface for communicating with the first medical pump, the data communicated between the first medical pump and the first server comprising data related to operation of the first medical pump, and a second interface for communicating with the second medical pump, data communicated between the second medical pump and the first server comprising data related to operation of the second medical pump;
   a second server comprising:
      memory for storing data, and
      a programmable circuit in electrical communication with the memory, the programmable circuit programmed with an interface for communicating with the at least one remote device, the data communicated between the at least one remote device and the second server comprising data related to operation of the first and second medical pumps;
   a computer network operably coupling the first server with the first medical pump, the first server with the second medical pump, the second server with the at least one remote device, and the first server with the second server; and
   a virtual connection between the first medical pump and the second medical pump, the virtual connection being coordinated by the first server such that at least one of the first medical pump or the second medical pump, receives data related to the other via the first server.

7. The system of claim 6 wherein the programmable circuit of the first server is further programmed to communicate text files with the first medical pump.

8. The system of claim 7 wherein the text files are coded with a markup language.

9. The system of claim 8 wherein the text files include text having a format selected from the group consisting of: hypertext markup language (HTML), standard generalized markup language (SGML), and eXtensible markup language (XML).

10. The system of claim 6 wherein the first medical pump is a pole-mounted pump.

11. The system of claim 6 wherein the programmable circuit of the first server further comprises a web server, wherein the web server includes a standardized interface adapted to communicate with a plurality of remote devices.

12. The system of claim 6 wherein the programmable circuit of the first server is further programmed to execute functions related to the operation and monitoring of the first and second medical pumps.

13. The system of claim 6 wherein the programmable circuit of the first server is further programmed to disable operation of the first medical pump.

14. The system of claim 6 wherein the programmable circuit of the first server is further programmed to enable operation of the first medical pump.

15. The system of claim 6 wherein the programmable circuit of the first server is further programmed, based on a set of programmed rules, to selectively associate the first medical pump with the second medical pump such that the first medical pump communicates with the second medical pump via the virtual connection and the first medical pump is configured to make operating decisions based on data related to the second medical pump.

16. The system of claim 15 wherein the programmable circuit of the first server is further programmed, based on a set of programmed rules, to selectively associate the first medical pump with a third medical pump wherein the first medical pump is configured to make operating decisions based on data related to the third medical pump and the virtual connection is further configured to establish a data link between the first medical pump and the third medical pump, the virtual connection being coordinated such that the first medical pump receives data related to the third medical pump.

17. The system of claim 6 wherein the data communicated between the first medical pump and the first server comprises an alerting state message related to the first medical pump, and the data communicated between the first medical pump and the first server further comprises an acknowledgment of the alerting state message.

18. The system of claim 6 wherein the second medical pump is a pole-mounted pump.

19. A method of programming a medical pump with a medical device server, the method comprising:
  receiving, by the medical device server, an initiation signal indicating an initiation of programming;
  sending a disable command to the medical pump to disable the medical pump from normal operation;
  programming operating parameters into the medical pump at the medical pump, while the medical pump is disabled;
  identifying that the medical pump programming is complete;
  receiving, by the medical device server, a programming complete signal from the medical pump; and
  sending, by the medical device server, an enable command to the medical pump to enable the medical pump to operate with the programmed operating parameters.

20. The method of claim 19 wherein identifying that the medical pump programming is complete comprises reviewing the programmed operating parameters.

21. A system for communicating between a clinician or other caregiver and a patient, the system comprising:
  a remote device configured to be operated by the clinician or other caregiver outside of a network accessible by the patient;
  a medical pump configured to be operated by the patient; and
  a medical device server comprising:
    memory configured to store data; and
    a programmable circuit in electrical communication with the memory, the programmable circuit comprising:
      a web server configured to interface with the remote device and the medical pump, and
      a display interface accessible to the remote device,
  wherein the remote device and the medical pump are operably coupled to the medical device server such that data related to the operation of the medical pump is received by the web server from the medical pump and displayed on the remote device by the display interface to facilitate the exchange of information between the clinician or other caregiver and the patient about the medical pump.

22. The system of claim 21, wherein the data related to the operation of the medical pump is received by the web server and stored in memory.

23. The system of claim 21, further comprising a patient remote device operated by the patient, wherein the web server is further configured to interface with the patient remote device, and the display interface is further accessible to the patient remote device.

* * * * *